US006692699B2

(12) United States Patent
Abbott et al.

(10) Patent No.: US 6,692,699 B2
(45) Date of Patent: Feb. 17, 2004

(54) BIOCHEMICAL BLOCKING LAYER FOR LIQUID CRYSTAL ASSAY

(75) Inventors: Nicholas L. Abbott, Madison, WI (US); Seung-Ryeol Kim, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/784,679

(22) Filed: Feb. 15, 2001

(65) Prior Publication Data

US 2002/0055093 A1 May 9, 2002

Related U.S. Application Data

(60) Provisional application No. 60/182,953, filed on Feb. 16, 2000.

(51) Int. Cl.[7] .............................. G01N 21/47; C12M 1/34

(52) U.S. Cl. ..................... 422/82.05; 422/55; 422/57; 422/68.01; 435/7.1; 435/287.8; 435/288.7

(58) Field of Search ........................ 422/55, 57, 58, 422/68.01, 82.01, 82.05, 102; 435/4, 7.1, 7.2, 7.4, 7.5, 287.1, 288.7, 287.8

(56) References Cited

U.S. PATENT DOCUMENTS

| 5,091,318 | A | * | 2/1992 | Anawis et al. | ............... | 436/513 |
| 5,712,103 | A | * | 1/1998 | Leavitt et al. | ............. | 435/69.6 |
| 6,171,802 | B1 | * | 1/2001 | Woolverton et al. | ......... | 435/7.1 |
| 6,284,197 | B1 | * | 9/2001 | Abbott et al. | ............ | 422/82.05 |

FOREIGN PATENT DOCUMENTS

| DE | 3617710 A1 | 12/1986 |
| EP | WO 99/63329 | 12/1999 |
| EP | WO 99/64862 | 12/1999 |
| JP | 02311822 | 12/1990 |
| JP | 02311824 | 12/1990 |
| JP | 03010222 | 1/1991 |
| JP | 03039932 | 2/1991 |
| JP | 04057024 | 2/1992 |
| JP | 04057025 | 2/1992 |
| JP | 04284423 | 10/1992 |
| JP | 05134257 | 5/1993 |
| JP | 05134258 | 5/1993 |
| JP | 06175136 | 6/1994 |
| JP | 06194513 | 7/1994 |
| JP | 06194662 | 7/1994 |

OTHER PUBLICATIONS

Weetall, Preparation of immobilized proteins covalently coupled through silane coupling agents to inorganic support, 1993, vol. 41, 157–188.*
Naoka, M, et al., Ferroelectric Liquid Crystal Alignment Films Utility Poly(DL amino acids) and Fibrous Proteins, Jun. 1999, Kobunshi Ronbunshu, 56(6):396–400.*
Weetall, Preparation of immobilized proteins covalently coupled through silane coupling agents to inorganic support, 1993, vol. 41, 157–188.*
Jerome, Surface effects and anchoring in liquid crystals, 1991, vol. 54, 391–451.*
Starkey, C.A. et al. "Evaluation of the Recombigen HIV–1 Latex Agglutionation Test", J. Clin. Microbiol., vol. 28, No. 4, Apr. 1990, pp. 819–822, published by the American Society for Microbiology.
Häussling, L. et al. "Biotin–Functionalized Self–Assembled Monolayers on Gold: Surface Plasmon Optical Studies of Specific Recognition Reactions", Langmuir, vol. 7, No. 9, Sep. 1991, pp. 1837–1840, published by the American Chemical Society (Washington, D.C.).
Schmitt, F.–J. et al. "Surface Plasmon Studies of Specific Recognition Reactions at Self–Assembled Monolayers on Gold", Thin Solid Films, vol. 210/211, (1992), pp. 815–817, published by Elsevier Sequoia.
Charych, D.H. et al. "Direct Colorimetric Detection of a Receptor–Ligand Interaction by a Polymerized Bilayer Assembly", Science, vol. 261, Jul. 30, 1993, pp. 585–588, published by the American Association for the Advancement of Science (Washington, D.C.).
Cocchi, J. M. et al. "Comparison Between Direct Binding, Competition and Agglutination Assays in the Characterization of Polyclonal Anti–idiotypes Against Anti–HBs Human Monoclonal Antibodies", Immunological Meth., vol. 160, 1993, pp. 1–9, Elsevier Science Publishers.
Kuby, J. Immunology, Second Edition (1994), pp. 147–150, W. H. Freeman and Company (New York, NY).
Cornell, B.A. et al. "A Biosensor that uses Ion–Channel Switches", Nature, vol. 387, Jun. 5, 1997, pp. 580–583, published by Nature Publishing (New York, NY).

(List continued on next page.)

*Primary Examiner*—Padmashri Ponnaluri
*Assistant Examiner*—My Chau Tran
(74) *Attorney, Agent, or Firm*—Foley & Lardner

(57) ABSTRACT

A rubbed substrate structure for use in a liquid crystal assay device, includes: a biochemical blocking compound chemically immobilized on a surface of one side of a support forming a biochemical blocking layer; and a biomolecule recognition agent deposited on the side of the support containing the biochemical blocking layer. The biomolecule recognition agent includes a recognition site capable of selectively recognizing a target species to be detected by the liquid crystal assay device. Additionally, the surface of the side of the support containing the biochemical blocking layer is rubbed such that it possesses features that drive a uniform anchoring of liquid crystals when the liquid crystals contact the side of the support containing the biochemical blocking layer. A method for preparing a rubbed substrate structure for use in a liquid crystal assay device, optical cells for use in a liquid crystal assay, liquid crystal assay devices, kits for use in a liquid crystal assay, and methods for detecting the presence of a target species using a liquid crystal assay device are also disclosed.

19 Claims, 12 Drawing Sheets

OTHER PUBLICATIONS

Lin, V. et al. "A Porous Silicon–Based Optical Interferometric Biosensor", Science, vol. 278, Oct. 31, 1997, pp. 840–843, published by the American Association for the Advancement of Science (Washington, D.C.).

Pan, J.J. et al. "Molecular Recognition and Colorimetric Detection of Cholera Toxin by Poly(diacetylene) Liposomes Incorporating Gm1 Ganglioside", Langmuir, vol. 13, No. 6, 1997, pp. 1365–1367, published by the American Chemical Society (Washington, D.C.).

Gupta, V. K. et al. "Optical Amplification of Ligand–Receptor Binding Using Liquid Crystals", Science, vol. 279, Mar. 27, 1998, pp. 2077–2080, published by the American Association for the Advancement of Science (Washington, D.C.).

Dancil, K.S. et al. "A Porous Silicon Optical Biosensor: Detection of Reversible Binding of IgG to a Protein A–Modified Surface", J. Am. Chem. Soc., vol. 121, 1999, pp. 7925–7930, published by the American Chemical Society (Washington, D.C.).

Kim, S–R., et al. "Orientation of Liquid Crystals on Mechanically Rubbed Films of Bovine Serum Albumin: A possible Substrate for Biomolecular Assays Based on Liquid Crystals", Anal. Chem., vol. 72, No. 19, Oct. 1, 2000, pp. 4646–4653, published by the American Chemical Society (Washington, D.C.).

* cited by examiner

○ = Rubbed Film
● = Unrubbed Film

○ = Rubbed immobilized BSA substrate
● = After 2 hour immersion in PBS-buffered 10 mg/mL BSA solution
□ = After 2 hour immersion in PBS-buffered 0.2 mg/mL fibrinogen solution
■ = After 2 hour immersion in PBS-buffered 100nM anti-BSA solution
△ = After 2 hour immersion in PBS-buffered 100nM anti-FITC solution ○ = Unrubbed film of immobilized biotin-BSA
● = Rubbed film of immobilized biotin-BSA ○ = Rubbing conditions of about 2.1 mm/second; 127 mm; and 1,000 Pa ● = Rubbing conditions of about 2.1 mm/second; 127 mm; and 250 Pa △ = Rubbing conditions of about 2.1 mm/second; 51 mm; and 250 Pa ○ = Rubbing conditions of about 2.1 mm/second; 127 mm; and 1,000 Pa
● = Rubbing conditions of about 2.1 mm/second; 127 mm; and 250 Pa
△ = Rubbing conditions of about 2.1 mm/second; 51 mm; and 250 Pa ○ = Rubbing conditions of about 2.1 mm/second; 127 mm; and 1,000 Pa
● = Rubbing conditions of about 2.1 mm/second; 127 mm; and 250 Pa
△ = Rubbing conditions of about 2.1 mm/second; 51 mm; and 250 Pa ○ = Increase in Thickness
● = Rubbed film of Biotin-BSA ○ = Increase in Thickness
● = Rubbed film of Biotin-BSA

BIOCHEMICAL BLOCKING LAYER FOR LIQUID CRYSTAL ASSAY

CROSS-REFERENCES TO RELATED APPLICATIONS

This application claims priority to U.S. Provisional Application No. 60/182,953, filed Feb. 16, 2000, the entire disclosure of which is incorporated herein by reference.

GOVERNMENT RIGHTS

This invention was made with United States government support awarded by the following agency: NSF 9632527. The United States has certain rights in this invention.

FIELD OF THE INVENTION

This invention pertains generally to the field of assays for biological and chemical substances and more specifically to blocking layers for use in liquid crystal assays.

BACKGROUND OF THE INVENTION

Methods for detecting the presence of biological substances and chemical compounds in samples has been an area of continuous development in the field of analytical chemistry and biochemistry. Various methods have been developed that allow for the detection of various target species in samples taken from sources such as the environment or a living organism. Detection of a target species is often necessary in clinical situations before a prescribed method of treatment may be undertaken and an illness diagnosed.

Several types of assay currently exist for detecting the presence of target species in samples. One conventional type of assay is the radioimmunoassay (RIA). RIA is a highly sensitive technique that can detect very low concentrations of antigen or antibody in a sample. RIA involves the competitive binding of radiolabeled antigen and unlabeled antigen to a high-affinity antibody. Typically, the labeled antigen is mixed with the antibody at a concentration that just saturates the antigen-binding sites of the antibody molecule. Then, increasing amounts of unlabeled antigen of unknown concentration are added. Because the antibody does not distinguish between labeled and unlabeled antigen, the two types of antigen compete for the available binding sites on the antibody. By measuring the amount of labeled antigen free in solutions, it is possible to determine the concentration of unlabeled antigen. Kuby, J., *Immunology*, W. H. Freeman and Company, New York, N.Y. (1991), pp. 147–150.

Another type of assay which has become increasingly popular for detecting the presence of pathogenic organisms is the enzyme-linked immunosorbent assay or ELISA. This type of assay allows pathogenic organisms to be detected using biological species capable of recognizing epitopes associated with proteins, viruses and bacteria. Generally, in an ELISA assay, an enzyme conjugated to an antibody will react with a colorless substrate to generate a colored reaction product if a target species is present in the sample. Kuby, J., *Immunology*, W. H. Freeman and Company, New York, N.Y. (1991), pp. 147–150. Physically adsorbed bovine serum albumin has been used in various such assays as a blocking layer because it has been found to prevent the non-specific adsorption of biological species that might interfere with or result in erroneous assay results.

Although ELISA and other immunosorbent assays are simple and widely used methods, they have several disadvantages. Tizard, I. R. *Veterinary Immunology: An Introduction*, W. B. Saunders Company, Philadelphia, Pa. (1996); Harlow, Ed.; Lane, D. *Antibodies: A Laboratory Manual*, Cold Springs Harbor Laboratory, Cold Springs Harbor, N.Y. (1988); Van Oss, C. J.; van Regenmortel, M. H. V. *Immunochemistry*, Dekker, New York, N.Y. (1994). Labeled antibodies can be expensive, especially for assays requiring radioactive labels. Additionally, radioactive labels require special handling as radioactive materials are also hazardous. The labeling of a compound, which is the main drawback of these methods, may alter the binding affinity of antibody to analyte. Enzymes are large molecules that may sterically inhibit antibody activity or it may lose enzymatic activity after conjugation to antibodies. Another concern with immunosorbent assays is non-specific binding of proteins to the solid support, antigen, and antibody complexes. This can lead to an increase in background noise, loss of sensitivity, and potentially a false positive test result. Additionally, the immobilization of proteins on the solid support can affect the conformation of the binding sites, leading to a decrease in sensitivity, and possible increase in non-specific binding. For example, physical adsorption of proteins to polystyrene wells occurs due to hydrophobic interactions between the protein and solid support. These interactions can also promote unfolding of the amino acid chains in order to cover the polystyrene surface. This can lead to possible inactivation of the binding sites.

Qualitative diagnostic assays based on aggregation of protein coated beads can also be used for the detection of proteins and viruses. Tizard, I. R. *Veterinary Immunology: An Introduction*, W. B. Saunders Company, Philadelphia, Pa. (1996): Cocchi, J. M.; Trabaud, M. A.; Grange, J.; Serres, P. F.; Desgranges, C. *J. Immunological Meth.*, 160, (1993), pp. 1; Starkey, C. A.; Yen-Lieberman, B.; Proffitt, M. R. *J. Clin. Microbiol.*, 28, (1990), pp. 819; Van Oss, C. J.; van Regenmortel, M. H. V. *Immunochemistry*, Dekker, New York, N.Y. (1994). For direct detection of antibodies, antigen is non-specifically adsorbed to the surface of latex beads which are several microns in diameter. The protein-coated beads possess a slight charge which prevents aggregation. Introduction of an antibody specific to the adsorbed protein can link the beads, leading to agglutination. The agglutination can be detected by eye or by other methods such as quasi-elastic light scattering. Visual agglutination assays, however, are not sensitive and measurement by quasi-elastic light scattering requires complex apparatus and is not suitable for use in locations remote from central labs. Furthermore, it is not possible to perform highly multiplexed agglutination assays using microarrays because of the bulk solution methodology of this type of assay.

To overcome the need for labeled proteins, principles based on direct detection of the binding of proteins and ligands have been investigated. Schmitt, F.-J.; Haussling, L.; Ringsdorf, H.; Knoll, W. *Thin Solid Films*, 210/211, (1992), pp. 815; Hauslling, L.; Ringsdorf, H. *Langmuir*, 7, (1991), pp. 1837. Surface plasmon reflectometry (SPR) is one such method. SPR is sensitive to changes in the index of refraction of a fluid near a thin metal surface that has been excited by evanescent electromagnetic waves. The binding of proteins to ligands can be detected by examining an increase in the resonance angle or intensity of signal. Typical angular resolution using this method is 0.005° allowing detection of sub-angstrom changes in adsorbed film thickness with SPR. However, care must be taken to ensure that the change in resonance angle is due to binding and not just a change in the bulk solution index of refraction. A thermally stable environment is required due to the dependence of the resonance angle on the index of refraction of the fluid. An increase in temperature from 25° C. to 26° C. in water amounts to a change in the index of refraction by 0.0001. This increase would result in the change in resonance angle of approximately 0.015° or roughly 0.2 nm in the observed height of a protein layer. This temperature stability requirement makes SPR unsuitable for most field applications. In addition, non-specific adsorption of molecules on to or near the sensor surface can lead to false changes in signal, requiring a surface which minimizes non-specific interactions. Therefore, surface plasmon reflectivity is more complex than ELISA, requires laboratory based equipment, and the preparation of a well defined surface.

The use of ion-channel switches for detecting biospecific interactions has been reported. Cornell, B. A.; Braach-Maksvytis, V. L. B.; King, L. G.; Osman, P. D. J.; Raguse, B.; Wieczorek, L.; Pace, R. J. Nature, 387, (1997), pp. 580. In a device using ion channel switches, a tethered lipid membrane incorporating mobile ion channels is separated from a gold electrode surface by an ion reservoir. The gold surface serves as an anchor for the membrane and acts as an electrode. Within the membrane are upper and lower ion channels. In order to become conductive, the outer and inner ion channels must align and form a dimer. Membrane spanning lipids, which help stabilize the lipid membrane, are attached at one end to the electrode surface and are terminated with ligands that extend away from the membrane. The ion channels of the outer layer possess ligands. Unbound, the outer ion channels move freely, occasionally forming dimers with the inner channels, allowing conduction. The binding of a bivalent molecule to both the ion channel and membrane spanning lipid restricts the mobility of the outer ion channel, leading to a measurable decrease in conductivity. However, if a large amount of protein adsorbs to the outer layer, the ion channel mobility presumably would be restricted and a false decrease in conductance could be observed due to non-specific interactions. Additionally, this method requires sensitive devices for detecting the change in conductance. The procedure for fabricating the membranes requires several hours and the membrane stability is limited (must be immersed in solution). More importantly, specific antibodies must be attached to the membrane/channels, requiring separate protein chemistry for each analyte to be detected.

A method based on a porous silicon support that permits optical detection of the binding of specific proteins to ligands has been reported. Lin, V.; Motesharei, K.; Dancil, K. S.; Sailor, M. J.; Ghadiri, M. R. Science, 278, (1997), pp. 840; Dancil, K. S.; Greiner, D. P.; Sailor M. J. J. Am. Chem. Soc., 121, (1999), pp. 7925. The porous areas are typically 1 to 5 μm deep and a few square micrometers to millimeters in area. Typical binding times are on the order of 30 minutes followed by rinsing of the surface. Initial work in this area incorrectly reported the detection of extremely low concentrations of analyte. Binding of streptavidin to biotinylated surfaces was initially found to reduce the index of refraction of the porous support, however this was later correctly attributed to surface oxidation. In addition, a change in the effective optical thickness of the film was reportedly observed upon introduction of streptavidin, however, differentiation between specific interactions and non-specific adsorption could not be made. This method does not require labeled molecules, however, the porous silicon surface is susceptible to oxidation and non-specific adsorption.

The use of polymerized multilayer assemblies for the detection of receptor-ligand interactions has also been reported. Charych, D. H.; Nagy, J. O.; Spevak, W.; Bednarski, M. D. Science, 261, (1993), pp. 585; Pan, J. J.; Charych, D. Langmuir, 13, (1997), pp. 1365. Polydiacetylene multilayer films deposited by Langmuir-Blodgett technique change color from blue to red due to a conformational change in the polymer backbone. For example, changes in temperature or pH can cause a shift in color. The response can be controlled and used for protein detection by attaching ligands to the multilayer. Upon binding of a multivalent macromolecule to ligands, stress is introduced into the multilayer assembly. A change in color is seen in the system if sufficient protein is bound, with binding times typically on the order of 30 minutes. This system permits direct detection of receptor-ligand interactions and transduces the events into an optical signal that can be easily measured and quantified. The optical output can be interpreted by eye or analyzed with a spectrophotometer for quantitative conclusions. The use of polymerized multilayer assemblies for the detection of influenza virus has been demonstrated. A significant disadvantage of this method, however, is that it requires multi-valent analyte. Multiple ligands connected to the polymerized multilayer must attach to the same macromolecule. This prevents the use of this method for monovalent molecules (even bead based assays can be performed competitively, not requiring multivalent molecules). Binding of bivalent molecules such as IgG's has not been demonstrated. Furthermore, Langmuir-Blodgett deposition is a process which is difficult to translate from laboratory to commercial scale. As an alternative method to Langmuir-Blodgett deposition, these principles has also been demonstrated using vesicles. However, research based on vesicles, reveals the usefulness of the system to be limited because it is insensitive to the analyte at concentrations below 0.1 mg/ml.

Although many of the conventional assay methods described above work very well to detect the presence of target species, many conventional assay methods are expensive and often require instrumentation and highly trained individuals, which makes them difficult to use routinely in the field. Thus, a need exists for assay devices and systems which are easier to use and which allow for evaluation of samples in remote locations.

Recently, assay devices that employ liquid crystals have been disclosed. For example, a liquid crystal assay device using mixed self-assembled monolayers (SAMs) containing octanethiol and biotin supported on an anisotropic gold film obliquely deposited on glass has recently been reported. Gupta, V. K.; Skaife, J. J.; Dubrovsky, T. B., Abbott N. L. Science, 279, (1998), pp. 2077–2079. In addition, PCT publication WO 99/63329 published on Dec. 9, 1999, discloses assay devices using SAMs attached to a substrate and liquid crystal layer that is anchored by the SAM.

Although the disclosed liquid crystal-based assay devices which use anisotropic gold films are suitable for use in determining whether a target species is present in a sample, the preparation of the anisotropic gold film by oblique deposition is difficult. For example, the preparation of obliquely deposited gold films requires complicated cleaning steps and high vacuum deposition. Therefore, a need exits for a substrate structure which is easy to prepare and which resists non-specific adsorption by proteins which could result in false positive test results.

SUMMARY OF THE INVENTION

The present invention provides rubbed substrate structures for use in a liquid assay device, optical cells prepared using the rubbed substrate structures, methods for preparing the rubbed substrate structures, kits for use in a liquid crystal assay, and methods for detecting a target species using a liquid crystal assay device.

A rubbed substrate structure for use in a liquid crystal assay device in accordance with the invention includes a biochemical blocking compound chemically immobilized on a surface of one side of a support forming a biochemical blocking layer and a biomolecule recognition agent deposited on the side of the support containing the biochemical blocking layer. The biomolecule recognition agent includes a recognition site capable of selectively recognizing a target species to be detected by the liquid crystal assay device. The surface of the side of the support containing the biochemical blocking layer and the deposited biomolecule recognition agent is rubbed such that it possesses features that drive a uniform anchoring of liquid crystals when the liquid crystals contact the side of the support containing the biochemical blocking layer and the deposited biomolecule recognition agent. In another preferred rubbed substrate structure, the surface of the side of the support containing the biochemical blocking layer is rubbed such that it possesses features that drive uniform anchoring of liquid crystals when the liquid crystals contact the side of the support containing the biochemical blocking layer, and the biomolecule recognition agent is deposited on the rubbed surface containing the biochemical blocking layer.

Another rubbed substrate structure for use in a liquid crystal assay device in accordance with the invention, includes: a biochemical blocking layer having biochemicals; a bifunctional spacer compound having a first end and a second end; a surface modifying compound having a first end and a second end; and a support having at least one side that contains the biochemical blocking layer. At least one of the biochemicals is covalently bonded to the first end of the bifunctional spacer compound through a first chemical reaction between a reactive group on the biochemical prior to the first chemical reaction and a reactive group on the first end of the bifunctional spacer compound prior to the first chemical reaction. The surface modifying compound is covalently bonded to the second end of the bifunctional spacer compound through a second chemical reaction between a reactive group on the first end of the surface modifying compound prior to the second chemical reaction and a reactive group on the second end of the bifunctional spacer compound prior to the second chemical reaction. Additionally, the surface modifying compound is covalently bonded to a surface on the side of the support containing the biochemical blocking layer through a third chemical reaction between a reactive group on the surface prior to the third chemical reaction and a reactive group on the second end of the surface modifying compound prior to the third chemical reaction. Finally, the side of the support containing the biochemical blocking layer is rubbed such that it possesses features that drive a uniform anchoring of liquid crystals when the liquid crystals contact the side of the support containing the biochemical blocking layer.

Preferred rubbed substrate structures as described above also include a biomolecule recognition agent deposited on the side of the support containing the biochemical blocking layer. The biomolecule recognition agent has a recognition site capable of selectively recognizing a target species to be detected by the liquid crystal assay device.

In preferred rubbed substrate structures, the bifunctional spacer compound is an organic compound having the following formula before the first and second chemical reactions:

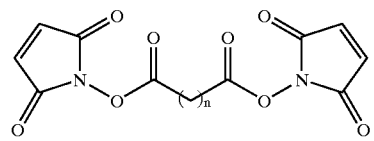

where n is an integer having a value ranging from 1 to 20, more preferably ranging from 2 to 10, or even more preferably ranging from 5 to 8. Most preferably, the bifunctional activating compound is disuccinimidyl suberate.

In other preferred rubbed substrate structures, the reactive group on the second end of the surface modifying compound before the third chemical reaction is a halogen-silicon bond or an alkoxy-silicon bond whereas in other preferred rubbed substrate structures, the surface modifying compound prior to the second and third chemical reactions is a silicon compound including a silicon atom; an alkoxy group bonded to the silicon atom through an oxygen-silicon bond; and an aminoalkyl group bonded to the silicon atom through a carbon-silicon bond. In still more preferred rubbed substrate structures, the surface modifying compound prior to the second and third chemical reactions is an aminoalkyltrialkoxysilane and more preferably is aminopropyltriethoxysilane.

In still other preferred rubbed substrate structures, the biochemicals of the biochemical blocking layer is a serum albumin, more preferably bovine serum albumin.

In still other preferred rubbed substrate structures the biomolecule recognition agent is an immunoglobulin or a portion of an immunoglobulin whereas in other preferred rubbed substrate structures, the biomolecule recognition agent is a peptide or carbohydrate or a sequence of peptides or carbohydrates, or sequences of DNA or RNA. In still other preferred rubbed substrate structures, the biomolecule recognition agent is capable of recognizing peptides, carbohydrates, DNA, RNA or fragments thereof, or a binding domain associated with a protein, a virus, a bacteria, or a microscopic pathogen.

Still other preferred rubbed substrates are provided in which at least two regions of the surface of the side of the support containing the biochemical blocking layer are rubbed under different pressures or for different lengths such that at least two regions of the surface of the side of the support containing the biochemical blocking layer have different sensitivities towards a target species.

A method for preparing a rubbed substrate structure suitable for use in a liquid crystal assay device includes reacting a biochemical blocking compound having at least one reactive group with an activated modified surface of a support. The activated modified surface of the support has at least one functional group capable of reacting with the reactive group of the biochemical blocking compound such that a covalent bond is formed between the biochemical and the support producing a support with a biochemical-blocking compound containing surface. The method also includes rubbing the biochemical-blocking compound containing surface of the support to produce a rubbed surface possessing features that drive the uniform anchoring of liquid crystals when the liquid crystals contact the rubbed surface.

Preferred methods for preparing a rubbed substrate structure suitable for use in a liquid crystal assay device also include reacting a surface modifying compound having a first end and a second end with a support such that a covalent bond between the support and the first end of the surface modifying compound is formed producing a surface modified support. Preferred methods also include reacting a bifunctional activating agent having a first end and a second end with the surface modified support such that a covalent bond is formed by reaction of the second end of the surface modifying agent with the first end of the bifunctional activating agent producing the activated modified surface of the support.

An optical cell for use in a liquid crystal assay device includes two rubbed substrate structures and a spacing material positioned between the biochemical blocking layers of the two rubbed substrate structures such that the biochemical blocking layer sides of the rubbed substrate structures face each other, but are separated by a cavity that can be filled with a liquid crystal.

A liquid crystal assay device according to the present invention includes a rubbed substrate structure; a surface that uniformly anchors liquid crystals; and a spacing material positioned between the biochemical blocking layer side of the rubbed substrate structure and the surface that uniformly anchors liquid crystals. The surface of the rubbed substrate structure includes both a biochemical blocking layer and a biomolecule recognition agent. In preferred liquid crystal assay devices, the surface that uniformly anchors liquid crystals may be another rubbed substrate structure with a biochemical blocking layer and a biomolecule recognition agent; a rubbed substrate structure that does not contain a biomolecule recognition agent; a glass slide treated with octadecyltrichlorosilane; a rubbed uncoated glass slide; a glass slide with shear-deposited Teflon on it; or a glass slide with an obliquely deposited gold film on it.

Kits for use in a liquid crystal assay include a rubbed substrate structure; a surface that uniformly anchors a liquid crystal; a spacing material, preferably a film, adapted to be placed between the rubbed substrate structure and the surface that uniformly anchors the liquid crystal; and a liquid crystal compound. In a preferred kit for use in a liquid crystal assay, the surface that uniformly anchors the liquid crystal is another rubbed substrate structure. In other preferred kits, the rubbed substrate structure, the surface that uniformly anchors the liquid crystal, and the spacing material are preassembled into a cell with the spacing material placed between them. In such a kit, the sample containing a possible target species would be flushed through the cell for a predetermined amount of time. Next, the liquid crystal would be placed in the cell and may be flushed through the cell, and the kit could thus be used to determine whether the target species was present in the sample.

A method for detecting the presence of a target species using a liquid crystal assay device includes incubating a rubbed substrate structure with a sample to be tested for the presence of the target species; placing a spacing material, preferably a film, between the incubated rubbed substrate structure and a surface that uniformly anchors liquid crystals such that the biochemical blocking layer side of the rubbed substrate structure faces the surface that uniformly anchors liquid crystals; drawing a liquid crystal into the area between the incubated rubbed substrate structure and the surface that uniformly anchors liquid crystals; and determining whether the liquid crystal is uniformly anchored on the rubbed substrate structure.

A device for detecting the presence of more than one target species in a sample is provided. The device includes a support with a rubbed surface having a biochemical blocking layer. The device also include a first target species detection region on a first portion of the support that has the biochemical blocking layer, and the first target species detection region has a first biomolecule recognition agent capable of binding the first target species. The device further includes at least one other target species detection region on at least one other portion of the support having the biochemical blocking layer, and the at least one other target species detection region has at least one other biomolecule recognition agent capable of binding the at least one other target species. The first target species detection region uniformly anchors liquid crystals in the absence of the target species, and the at least one other target species detection region uniformly anchors liquid crystals in the absence of the at least one other target species. The uniform anchoring of liquid crystals in the first target species detection region is disrupted when the first target species detection region is exposed to the first target species, and the uniform anchoring of liquid crystals in the at least one other target species detection region is disrupted when the at least one other target species detection region is exposed to the at least one other target species.

Particularly preferred devices for determining the presence of a target species in a sample are included in which the surface is rubbed while the first biomolecule recognition agent and the at least one other biomolecule recognition agent are respectively present in the first target species detection region and the at least one other target species detection region.

The invention further provides kits for use in detecting the presence of a target species in a sample which kits include at least one rubbed substrate structure and a liquid crystal compound. A method of detecting the presence of a target species in a sample using this type of kit is also provided. The method includes contacting a portion of the rubbed substrate of the kit with a quantity of the sample; placing the liquid crystal of the kit on the portion of the rubbed substrate structure that had contacted the sample; and determining whether the uniform anchoring of the liquid crystal has been disrupted.

Further objects, features and advantages of the invention will be apparent from the following detailed description when taken in conjunction with the accompanying drawings.

DETAILED DESCRIPTION OF THE INVENTION

Figure 1:
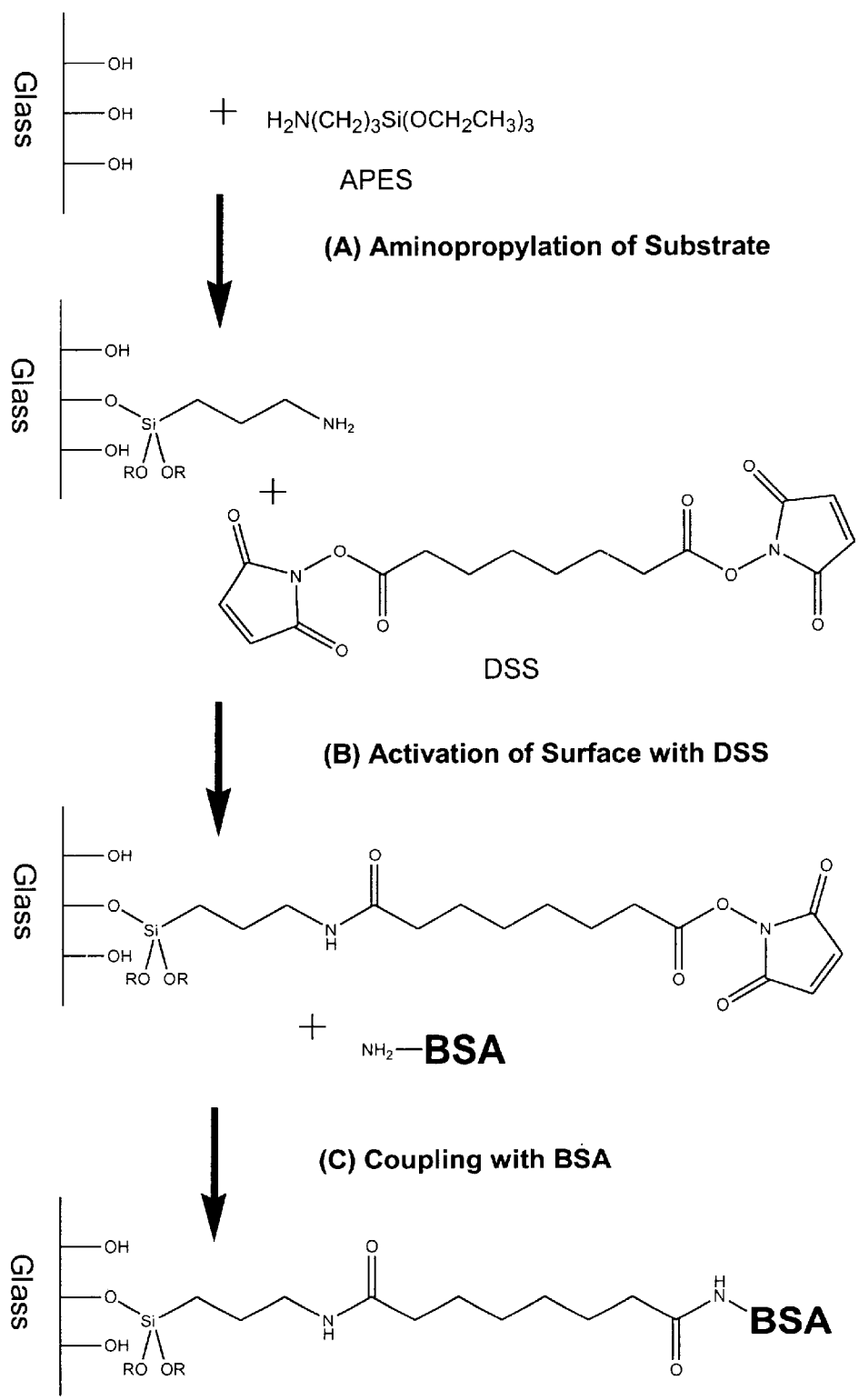
FIG. 1 is a schematic diagram showing various steps used to chemically bond bovine serum albumin (BSA) to a glass plate. First, a clean and dry glass slide is silylated with 3-aminopropyltriethoxysilane. Second, one side of a bifunctional cross-linking agent such as disuccinimidyl suberate (DSS) is reacted with the silylated glass slide to provide an activated surface for reaction with the amine group of bovine serum albumin. Finally, the BSA is reacted with the free end and reactive side of the attached DSS to provide a stable amide bond that secures the BSA to the glass as shown in the Figure.

The following abbreviations are used throughout this application:

| | |
|---|---|
| APES: | 3-Aminopropyltriethoxysilane |
| BSA: | Bovine Serum Albumin |
| DMSO: | Dimethyl sulfoxide |
| DSS: | Disuccinimidyl suberate |
| OTS: | Octadecyltrichlorosilane |
| PBS: | Phosphate-buffered saline |
| 5CB: | 4-Cyano-4'-pentylbiphenyl |

All ranges recited herein include all combinations and subcombinations included within that range's limits. Therefore, a range from "5–92%" includes ranges from "5–84%", "16–75%", etc. A range of "less than 1000 Pa" would include "less than 400 Pa", "less than 250 Pa", etc.

Generally, the invention provides rubbed substrate structures for use in liquid crystal assay devices; methods for preparing rubbed substrate structures; optical cells prepared from rubbed substrate structures; kits containing rubbed substrate structures; and methods for detecting the presence of a target species using a liquid crystal assay device.

Rubbed substrates should possess specific characteristics if they are to be useful in specifically binding biological target molecules and drive reorientation in the liquid crystals. The reorientation of the liquid crystals is necessary as this is what allows an assay device assembled from rubbed substrate structures to be used to determine whether a target species is present in a given sample. Some of the characteristics which a suitable rubbed substrate should possess include: the ability to resist non-specific adsorption; the ability to orient liquid crystals uniformly; and the possession of anisotropic structure that the specific binding of the target species can partially or completely erase. The latter characteristic drives the non-uniform anchoring of liquid crystals which indicates that the target species is present in the sample.

Rubbed biochemical blocking layers such as rubbed BSA resist the non-specific adsorption of other species such as proteins. Additionally, a rubbed substrate containing such a rubbed blocking layer provides uniform alignment of liquid crystals which can be disrupted when a target species binds to a biomolecule recognition agent on the surface.

Rubbed substrate structures for use in liquid crystal assay devices generally include a biochemical blocking compound immobilized on the surface of at least one side of a support. The immobilization of the biochemical blocking compound on the support forms a biochemical blocking layer on the support.

A wide variety of materials may be used as supports in the rubbed substrate structures according to the present invention as will be apparent to those skilled in the art. Preferred supports include polymers and silica-containing materials that contain hydroxyl groups for reaction with surface modifying compounds or agents. Examples of polymeric supports include, but are not limited to, polystyrene, polycarbonates, and polymethyl methacrylate which are preferably plasma treated to present hydroxyl or carboxylic acid functionalities. Other materials suitable for use as supports include metal oxides such as, but not limited to, indium oxide, tin oxide, and magnesium oxide and metals such as, but not limited to, gold, silver, and platinum which are preferably reacted with a sulfur-containing compound that contains a reactive functionality such as a hydroxyl or carboxylic acid group. Still other materials that may be used as supports include cellulosic materials such as nitrocellulose, wood, paper, and cardboard and sol-gel materials. Especially preferred supports include glass, quartz, and silica, and most preferred supports include glass slides and silica wafers. Preferably, such supports are cleaned prior to use. For example, glass slides are preferably cleaned by treatment in "piranha solution" (70% $H_2SO_4$/30% $H_2O_2$) for 1 hour and then rinsed with deionized water before drying under a stream of nitrogen. "Piranha solution" requires care in handling as it reacts violently with organic compounds and should not be stored in closed containers.

Various materials such as, but not limited to, serum albumins, zwitterionic polymers, adsorbed lipid layers, dextran and other sugars, cross-linked lipids, polyethyleneoxide, polyoxazolines, and hydrogels may be suitable for use as biochemical compounds for use in the biochemical blocking layer. Preferred materials for use as biochemical blocking compounds include serum albumins such as, but not limited to, bovine serum albumin, human serum albumin, rodent serum albumin, canine serum albumin, feline serum albumin, porcine serum albumin, equine serum albumin, and rabbit serum albumin. Bovine serum albumin is a particularly preferred biochemical blocking compound for use in forming a biochemical blocking layer in a rubbed substrate structure according to the present invention.

A rubbed substrate structure for use in a liquid crystal assay device preferably includes a biomolecule recognition agent which is deposited on a side of the support that contains the biochemical blocking layer. The biomolecule recognition agent includes a recognition site capable of recognizing and preferably binding a target species to be detected by the liquid crystal assay device if the target species is present in a sample.

The biochemical blocking compound may be placed on the support using physical adsorption without chemically immobilizing the biochemical blocking compound on the support. For example, a glass slide or silicon wafer support may be immersed in a PBS-buffered BSA solution overnight and then dried. Such BSA-coated supports may be prepared using various supports including, but not limited to, untreated clean glass slides and OTS-treated glass slides.

More preferably, the biochemical blocking layer is chemically immobilized on the surface of the support. This may be accomplished by treating a biochemical blocking layer physically adsorbed on a support with a crosslinking agent such as, but not limited to, glutaraldehyde. More preferably, a surface modifying agent is used in conjunction with a bifunctional spacer compound or activating agent to secure the biochemical blocking compound to the surface of the support.

FIG. 1 is a reaction scheme showing the steps that are preferably used in a process for chemically immobilizing a biochemical blocking layer onto the surface of a support for use in a liquid crystal assay device. As shown in FIG. 1, a support is generally first treated with a surface modifying agent having one end bearing a reactive group capable of reacting with a functional group on the surface of the support and another end having a reactive group capable of reacting with a reactive group on one end of the bifunctional spacer compound. In preferred surface modifying compounds, the reactive group capable of reacting with the functional group of the support includes functionalities such as, but not limited to, a halogen-silicon bond or an alkoxy-silicon bond. These functionalities react with the hydroxyl groups on supports such as silica wafers or glass to form a covalent bond tethering the silicon compound to the surface of the support. Preferred surface modifying compounds also include an end with a reactive group capable of reacting with a reactive group on one end of the bifunctional spacer compound. Preferred such reactive groups on the surface modifying compound include, but are not limited to alkylamines. Thus, preferred surface modifying agents are silicon compounds which include a silicon atom; at least one alkoxy group bonded to the silicon atom through an oxygen-silicon bond; and an aminoalkyl group bonded to the silicon atoms through a carbon-silicon bond. More preferred surface modifying compounds include aminoalkyltrialkoxysilanes such as those having aminoalkyl groups having from 2 to 8 carbon atoms. An especially preferred such compound is aminopropyltriethoxysilane (APES).

Those skilled in the art will recognize that alkoxy groups such as methoxy, propoxy, butoxy, and pentoxy may be used in place of the ethoxy groups. Additionally, those skilled in the art will recognize that other silanes such as, but not limited to, aminoalkyldialkylchlorosilanes, sulfhydryl-terminated silanes such as 3-mercaptopropyltrimethoxysilane, and silanes with double bonds such as allyltrichlorosilane and allyltrialkoxysilanes may also be used as the surface modifying compound. Those skilled in the art will recognize that silanes with sulfhydryl groups such as 3-mercaptopropyltrimethoxysilane would react with both the surface hydroxyl groups on the support and with the biochemical blocking compound via formation of a disulfide bond between the sulfhydryl group on the silane and a sulfhydryl group on the protein. Thus, a bifunctional spacer compound might not be necessary if such a surface modifying compound were employed. However, if desired, a heterobifunctional cross linker such as n-succinimidyl 3-(2-pyridylthio)propionate (SPDP) or succinimidyloxycarbonyl-methyl-(2-pyridylthio)toluene (SMPT), or succinimidyl-4-(N-maleimido-methyl) cyclohexane-1-carboxylate (SMCC) or maleimidobenzoyl-N-hydroxysuccinimide ester (MBS) could be used with such a sulfhydryl containing surface modifying silicon compound.

Reaction between the surface modifying compound and the support produces a support with a modified surface that can be activated by reaction with the bifunctional spacer compound. Because water in the reaction mixture may result in an undesirable reaction with the surface modifying compound, the reaction between the surface modifying compound and the support is preferably conducted using anhydrous solvents and conditions although those skilled in the art will recognize that the presence of some water will be tolerated.

In the process for chemically immobilizing a biochemical blocking layer on the surface of a support, a reactive group on one end of a bifunctional spacer compound or bifunctional activating agent is typically reacted with the modified surface to activate the surface forming an activated modified surface of the support. Preferred bifunctional spacer compounds have two ends that may have similar or different functional groups. Preferred such bifunctional spacer compounds will have leaving groups at each of two ends so that one end will react with a group such as an amine on the biochemical blocking compound and the other end will react with a group such as an amine group on the tethered surface modifying compound. Preferred bifunctional spacer compounds or activating agents include structures having the following formula:

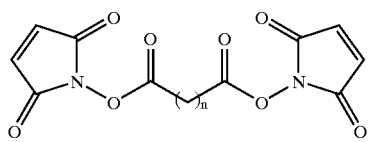

where n is an integer having a value ranging from 1 to 20, more preferably ranging from 2 to 10, or even more preferably ranging from 5 to 8. Most preferably, the bifunctional spacer compound or activating agent is disuccinimidyl suberate where n has a value of 6.

Those skilled in the art will recognize that a wide variety of bifunctional spacer compounds may be used in place of the above disuccinimidyl species and will prove effective in immobilizing biochemical blocking compounds on the surfaces of supports. Examples of homobifunctional spacer compounds that would react with an amine on the surface modifying compound and an amine on the biochemical compound of the biochemical blocking layer include, but are not limited to: disuccinimidyl suberate; bis (sulfosuccinimidyl) suberate; disuccinimidyl glutarate; dimethyl adipimidate; dimethyl suberimidate; dimethyl pimelimidate; dimethyl 3,3-dithiobispropionimidate; methyl N-succinimidyl adipate; and 1,5-difluoro-2,4-nitrobenzene. Examples of homobifunctional spacer compounds that would react with a sulfhydryl group on the surface modifying compound and a sulflhydryl group on the biochemical compound of the biochemical blocking layer include, but are not limited to: 1,11-bis-maleimidotetraethyleneglycol; bis-maleimidohexane; 1,6-hexane-bis-vinylsulfone; 1,8-bis-maleimidotriethylene glycol; 1,4-bis-maleimidobutane; and bismaleimidoethane.

In addition to the homobifunctional spacer compounds presented above, it is possible to use heterobifunctional spacer compounds in the present invention. Examples of bifunctional spacer compounds with one end capable of reacting with an amine and one end capable of reacting with a sulfhydryl include, but are not limited to: N-(κ-maleimidoundecanoyloxy) sulfosuccinimide ester; succiminidyl-4-(N-maleimidomethyl)cyclohexane-1-carboxy-(6-amido-caproate); N-(κ-maleimidoundecanoic acid); succinimidyl 4-[p-maleimidophenyl]butyrate; succinimidyl-6[(β-maleimidopropionamido)hexanoate]; succinimidyl 4-(N-maleimidomethyl)cyclohexane-1-carboxylate; N-succinimidyl(4-iodoacetyl)aminobenzoate; N-[γ-maleimidobutyryloxy]succinimide ester; m-maleimidobenzoyl-N-hydroxysuccinimide ester; N-ε-maleimidocaproic acid; N-[ε-maleimidocaproyloxy] succinimide ester; N-succininidyl-[4-vinylsulfonyl] benzoate; N-[β-maleimidopropyloxy]-succinimide ester; succinimidyl 3-[bromoacetamido]propionate; N-β-maleimidopropionic acid; N-[α-maleimidoacetoxy] succinimide ester; N-succinimidyl S-acetylthiopropionate; and N-succinimidyl iodoacetate. A bifunctional spacer compound with one end capable of reacting with an amine and one end capable of reacting with a carboxyl group includes 1-ethyl-3-(3-dimethylaminopropyl)carbodiimide hydrochloride. An example of a heterobifunctional spacer compound with one end capable of reacting with a sulfhydryl group and one end capable of reacting with a hydroxyl group includes N-[p-maleimidophenyl]isocyanate.

The biochemical blocking compound is preferably reacted with the activated modified surface of the support produced by reaction with the bifunctional spacer compound. For example, one of the amine groups, preferably an amine such as an ε-amino group on a lysine residue, will be reacted with the unreacted end of the bifunctional spacer compound to form a covalent amide bond immobilizing the biochemical blocking compound on the surface of the support.

As noted above, the biomolecule recognition agent is deposited on the side of the support containing the biochemical blocking layer. The biomolecule recognition agent may be deposited before, during, or after the biochemical blocking layer has been immobilized on the surface of the support. While the biomolecule recognition agent may be adsorbed on the surface of the support, preferably it will also be chemically immobilized on the surface of the support or attached, by bonding or otherwise, to the biochemical blocking layer. Preferred biomolecule recognition agents include immunoglobulins such as IgGs or portions of immunoglobulins that are more preferably capable of recognizing and binding epitopes and binding domains associated with proteins, viruses, bacteria, and other microscopic pathogens. Other preferred biomolecule recognition agents include peptides or sequences of peptides, proteins, carbohydrates or sequences of carbohydrates, RNA and DNA. Other preferred biomolecule recognition agents are capable of recognizing and binding peptide sequences, proteins, carbohydrates and sequences of carbohydrates, DNA, RNA, or fragments of RNA or DNA. Preferably, an amine group on the biomolecule recognition agent will be reacted with the activated modified surface of the support and then the biochemical blocking compound will be added and immobilized on the surface of the support. Small molecules may serve as biomolecule recognition agents. For example, a small molecule such as biotin may be tethered to the rubbed surface of a biochemical blocking layer such as BSA to specifically bind a protein. Thus, a rubbed substrate with such a biomolecule recognition agent could be used to screen small molecule-protein interactions that would be useful in drug discovery processes.

As noted above, the biomolecule recognition agent may be placed on the surface of a rubbed substrate structure using various methods. For example the activated surface containing the DSS may first be treated with an immunoglobulin and then subsequently may be reacted with the biochemical compound making up the blocking layer. In another procedure, the activated surface containing the DSS may be reacted with a biochemical blocking compound such as BSA and then rubbed. Such a rubbed surface may then be treated with DSS and a ligand terminated with an amine group such as biotin, peptides, polypeptides, and DNA or RNA and fragmentary sequences of these. These would then be immobilized on the rubbed BSA surface. In still another procedure, the activated surface containing the bound DSS may be partially reacted with BSA and then rubbed. The resulting structure could then be immersed in a solution containing an immunoglobulin. In still another procedure, a DSS-activated surface is reacted with a protein. The surface with the protein on it is then immersed into an immunoglobulin-containing solution and then into a solution containing a biochemical blocking compound such as BSA. In a particularly preferred procedure, an activated surface containing an activating agent such as, but not limited to DSS, is reacted with a biochemical blocking compound that is bonded to a biomolecule recognition agent such as, but not limited to, biotinylated BSA. This produces a substrate containing both a biochemical blocking compound and a biomolecule recognition agent which may be rubbed to induce uniform anchoring of a liquid crystal such as, but not limited to, 5CB. A rubbed substrate such as that prepared from biotin-BSA may be used to prepare optical cells and kits for detecting the presence of anti-biotin IgG. It will be apparent to those skilled in the art that various biomolecules recognition agents and biochemical blocking compounds may be attached to a support in the fashion described above to produce a substrate that may be rubbed and which will then exhibit non-uniform anchoring of liquid crystals upon exposure to specific target species that bind to the biomolecule recognition agent.

According to one preferred procedure, a biochemical blocking compound with a biomolecule recognition agent attached to it is delivered to a specific portion of an activated surface as a droplet of liquid. In this manner, the biochemical blocking compound with a particular biomolecule recognition agent is confined to only a particular localized area of the surface. A second drop of liquid containing the biochemical blocking agent functionalized with a recognition agent that is different from the first is placed at a second location on the surface. This procedure is repeated until the surface supports an array of areas, each of which is covered by the blocking agent and a different recognition agent. The whole surface could then be rubbed. This procedure provides a surface suitable for use as a biochemical microarray and permits the detection of a multiplicity of species within a sample. Those skilled in the art will recognize that variations on the above procedure could also be used to produce a multiarray. In one such preferred procedure, rather than "spotting" droplets of liquid on a surface, a fluidic channel (e.g., made from micromolded polydimethylsiloxane) is used to deliver liquids to localized regions of a surface. Generally, any method known to those skilled in the art for delivering liquids to localized regions of a surface could be used to produce the preferred microarray devices for detection of multiple target species.

The microarray presented above provides a device for detecting the presence of more than one target species in a sample. The device includes a support with a rubbed surface having a biochemical blocking layer. The device also include a first target species detection region on a first portion of the support that has the biochemical blocking layer, and the first target species detection region has a first biomolecule recognition agent capable of binding the first target species. The device further includes at least one other target species detection region on at least one other portion of the support having the biochemical blocking layer, and the at least one other target species detection region has at least one other biomolecule recognition agent capable of binding the at least one other target species. The first target species detection region uniformly anchors liquid crystals in the absence of the target species, and the at least one other target species detection region uniformly anchors liquid crystals in the absence of the at least one other target species. The uniform anchoring of liquid crystals in the first target species detection region is disrupted when the first target species detection region is exposed to the first target species, and the uniform anchoring of liquid crystals in the at least one other target species detection region is disrupted when the at least one other target species detection region is exposed to the at least one other target species.

Particularly preferred devices for determining the presence of a target species in a sample are included in which the surface is rubbed while the first biomolecule recognition agent and the at least one other biomolecule recognition agent are respectively present in the first target species detection region and the at least one other target species detection region.

The surface of the substrate containing the biochemical blocking layer is rubbed in, preferably, but not limited to, one direction. For some procedures, it is desirable to rub different regions of the biochemical blocking layer in different directions. This permits the creation of a pattern in the liquid crystal upon binding of biochemicals to the recognition moiety. This pattern might be used to provide information to the user. For some procedures it is also desirable to rub the biochemical blocking layer in small sections using different rubbing conditions in each region. This permits the preparation of a surface on which there will exist a range of sensitivities to the bound target biochemical. Generally, the surface of the substrate is rubbed so that the surface possesses features that drive a uniform anchoring of liquid crystals in the absence of a material which binds to the surface and disrupts the uniform anchoring of the liquid crystals when the liquid crystals contact the side of the support containing the biochemical blocking layer. Those skilled in the art will recognize that the rubbing of the substrate structure may be performed using various devices and apparatuses and various rubbing materials including, but not limited to, a velvet-type polyester cloth, silk, velvet, cotton, wool, tissue paper, canvas, nylon, and polyester. A preferred rubbing material is a velvet-type polyester cloth. Methods of rubbing include, but are not limited to: pushing a hand-held cloth across the surface of a substrate; fitting a device similar to a mechanical sander for use in sanding wood with cloth and holding it against the surface of a substrate; and rotating a cloth attached to a cylindrical roller above a substrate and then lowering the rotating cylinder down onto the substrate. Those skilled in the art will realize that there are many methods that can be used to rub surfaces such that the surfaces uniformly orient liquid crystals including those methods developed for the rubbing of surfaces for use in liquid-crystal-based computer displays. Generally, rubbing the substrate involves forcing a cloth or other material across the substrate surface while the cloth contacts the surface.

Figure 2:
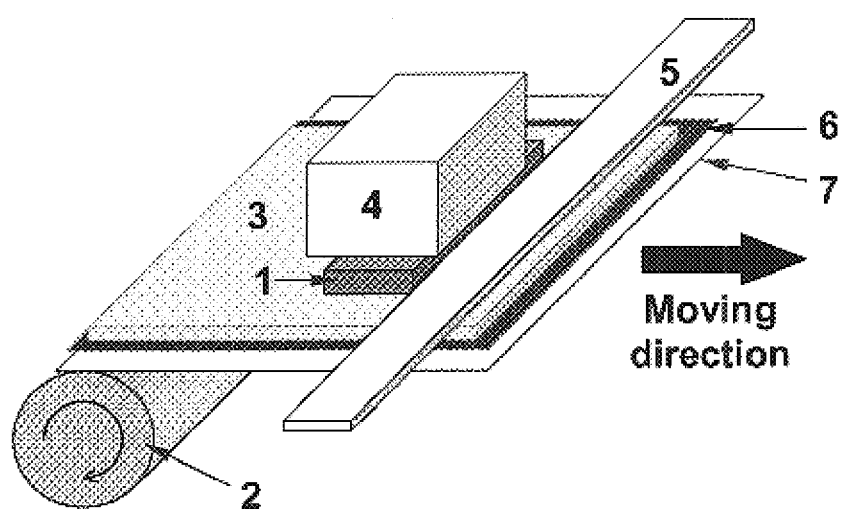
FIG. 2 is a diagram showing the apparatus used to rub glass slides and silicon wafers prepared using the procedure shown in FIG. 1. Various parts of the apparatus include a glass slide 1; a motorized rubbing machine 2 (a modified strip chart recorder); a velvet-type polyester cloth rubbing material 3; an aluminum block weight 4; a fixed stopper 5; double-sided tape 6; and chart paper as the moving guide 7.

One method for rubbing the surface of the substrate containing the biochemical blocking layer uses a modified strip chart recorder such as that shown in FIG. 2. As shown in FIG. 2, a slide 1 was typically placed on a modified strip chart recorder 2 so that the side of slide 1 containing the biochemical blocking layer faced down on the rubbing material 3. An aluminum weight 4 was then placed on the slide to provide pressure on slide 1 which was held in place with a fixed stopping device 5. Double-sided tape 6 was typically used to secure the rubbing material to the top of the chart paper 7 used as the moving guide. Rubbing was preferably accomplished using an applied pressure of from about 250 to about 1,000 Pa. The movement of the rubbing material was typically about 5 mm/sec to about 2.1 mm/sec, and rubbing was typically conducted for a period of from about 1 minute to about 30 seconds. Those skilled in the art will recognize that various pressures, times, and speeds may be used to rub the substrate structures. However, as described below, it has been surprisingly and unexpectedly discovered that the sensitivity of optical cells for biochemical detection prepared from rubbed substrates can be modified significantly by changing the rubbing speed, rubbing length, and rubbing pressure. Rubbing pressure and rubbing length, in particular, have been found to impact sensitivity. A decrease in the pressure used to rub the substrate has been found to greatly increase the sensitivity of the rubbed substrate towards the anchoring of liquid crystals at a given concentration of species to be detected. The same is true with respect to rubbing length.

The biochemical blocking layer resists the non-specific adsorption of non-target species. Any non-specific adsorption of non-target species that does occur, does not change in the orientation of a liquid crystal on the surface such that it prevents the interpretation of the orientation of the liquid crystal so as to infer the binding of the targeted species. For example, rubbed substrate structures on silicon wafers or glass slides containing a biochemical blocking layer formed from bovine serum albumin resisted the non-specific adsorption of fibrinogen, lysozyme, anti-FITC, and anti-streptavidin. This important characteristic of the biochemical blocking layer is important in rubbed substrate structures for employment in liquid crystal assay devices because non-specific adsorption of non-target species would disrupt the uniform anchoring of liquid crystals brought into contact with the surface which would result in a false positive test result. A particularly preferred biochemical blocking layer contains BSA which resists non-specific adsorption, has numerous cites for attachment of biomolecule recognition agents, reacts easily with activated surfaces of supports, and rubs to produce uniform anchoring of liquid crystals such as 5CB.

TABLE 1

Molecular structure of mesogens suitable for use in Liquid Crystal Assay Devices

| Mesogen | Structure |
|---|---|
| Anisaldazine | $CH_3-O-\bigcirc-CH=N-N=CH-\bigcirc-O-CH_3$ |
| NCB | $C_nH_{2n+1}-\bigcirc-\bigcirc-CN$ |
| CBOOA | $C_9H_{19}-O-\bigcirc-N=CH-\bigcirc-CN$ |
| Comp A | $C_7H_{15}-\bigcirc-\bigcirc-COO-\bigcirc-NCS$ |
| Comp B | $C_8H_{17}-O-\bigcirc-O-CO-\bigcirc-O-CH_2-\bigcirc-CN$ |
| $DB_7NO_2$ | $C_7H_{15}-\bigcirc-O-CO-\bigcirc-O-CO-\bigcirc-NO_2$ |
| DOBAMBC | $C_{10}H_{21}-O-\bigcirc-CH=N-\bigcirc-CH=CH-COO-CH_2-CH(CH_3)(C_2H_5)$ |
| nOm<br>n = 1, m = 4: MBBA<br>n = 2, m = 4: EBBA | $C_nH_{2n+1}-O-\bigcirc-CH=N-\bigcirc-C_mH_{2m+1}$ |
| nOBA<br>n = 8: OOBA<br>n = 9: NOBA | $C_nH_{2n+1}-O-\bigcirc-COOH$ |

TABLE 1-continued

Molecular structure of mesogens suitable for use in Liquid Crystal Assay Devices

| Mesogen | Structure |
|---|---|
| nmOBC | 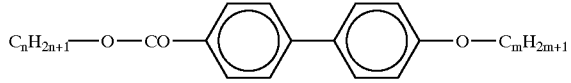 |
| nOCB | 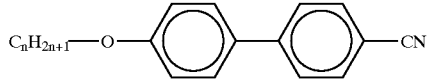 |
| nOSI | 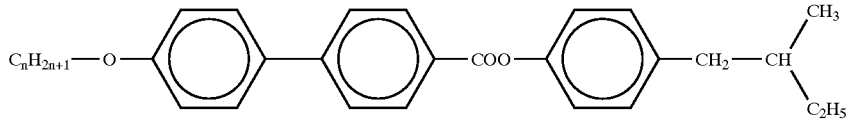 |
| 98P | 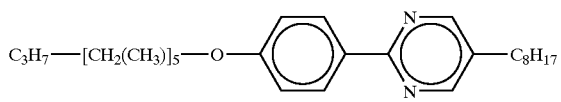 |
| PAA | 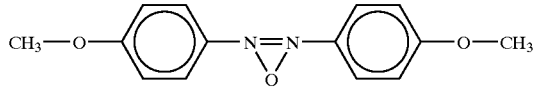 |
| PYP906 | 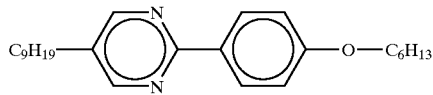 |
| nSm | 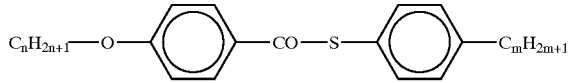 |

Various types of liquid crystals may be used in conjunction with the rubbed substrate structures. Examples of these include both nematic and smectic liquid crystals. Other classes of liquid crystals that may be used in accordance with the invention include, but are not limited to: polymeric liquid crystals, lyotropic liquid crystals, thermotropic liquid crystals, columnar liquid crystals, nematic discotic liquid crystals, calamitic nematic liquid crystals, ferroelectric liquid crystals, discoid liquid crystals, and cholesteric liquid crystals. Examples of just some of the liquid crystals that may be used are shown above in Table 1. A particularly preferred liquid crystal for use in the present invention includes 4-cyano-4'pentylbiphenyl.

An optical cell for use in a liquid crystal assay device preferably includes two rubbed substrates as described above and a spacing material, preferably a film, which is positioned between the two rubbed substrates to create a cavity that can be filled with a liquid crystal. Other preferred optical cells according to the present invention include a rubbed substrate structure such as that described above; a surface that uniformly anchors liquid crystals; and a spacing material positioned between the biochemical blocking layer side of the rubbed substrate structure and the surface that uniformly anchors liquid crystals. Thus, it is not required that both surfaces of the optical cell be rubbed substrates. The spacing material is preferably a film of a defined thickness that is more preferably stable in the presence of the liquid crystal material, easy to handle, and does not contaminate the liquid crystal. A variety of films may be suitable for use as spacing materials in the optical cells according to the invention as will be apparent to those skilled in the art. However, a preferred film spacing material is preferably made of a polymeric material such as Mylar® film or Saran® wrap. The film spacing material is typically placed between the rubbed substrates such that a surface of each of the rubbed substrates containing the biochemical blocking layer faces another such surface on the other rubbed substrate. The spacing material may also be comprised of microspheres or rods of defined diameter that are dispersed into the liquid crystal so as to separate the two surfaces forming the optical cell.

A liquid crystal assay device according to the present invention includes a rubbed substrate structure such as that described above; a surface that uniformly anchors liquid crystals; and a spacing material positioned between the biochemical blocking layer side of the rubbed substrate structure and the surface that uniformly anchors liquid crystals. The surface of the rubbed substrate structure includes both a biochemical blocking layer and a biomolecule recognition agent. The side of the rubbed substrate structure that contains the biochemical blocking layer and the surface that uniformly anchors liquid crystals face each other and are separated by a spacing agent positioned between them. The liquid crystal is drawn into the area between the rubbed substrate structure and the surface that uniformly anchors liquid crystals. In preferred assay devices, the surface that uniformly anchors liquid crystal is also a rubbed substrate structure which may also contain a biomolecule recognition agent although this is not necessary. Other materials suitable for use as the surface that uniformly anchors liquid crystals include glass surfaces modified by reaction with octadecyltrichlorosilane and glass surfaces with obliquely deposited gold films. Other suitable surfaces that uniformly anchor liquid crystals include rubbed glass slides and glass slides with shear-deposited Teflon. As long as the surface uniformly anchors liquid crystals, the presence of a target species in a sample will disrupt the anchoring of the liquid crystal in the rubbed substrate structure with the biomolecule recognition agent and will thus be detected.

Kits for use in a liquid crystal assay typically contain a rubbed substrate structure according to the invention; a surface that uniformly anchors liquid crystals; a spacing material such as a film adapted to be placed between the rubbed substrate structure and the surface that uniformly anchors liquid crystals such that an assay device, as described above, may be manufactured; and a liquid crystal. The surface that uniformly anchors liquid crystals may be a rubbed substrate or another surface that uniformly anchors liquid crystals such as those described above. Such kits may include instructions for the detection of a target species. Such instructions will typically include directions for incubating the rubbed substrate with a sample that possibly contains a target species to be detected. It will also preferably contain instructions explaining how the presence of the target species is identified and may also contain steps that may be used to determine the concentration of the target species in a sample. Furthermore, preferred kits may contain rubbed substrates prepared using varying rubbing conditions that may be used to detect the presence of target species at varying concentrations. In some preferred kits, the rubbed substrate structure, the surface that uniformly anchors liquid crystals which may be another rubbed substrate structure, and the spacing material are preassembled into an optical cell. In such a kit, a sample to be tested for a target species may be drawn or flowed through the preassembled cell followed by the liquid crystal. Such kits may thus also contain one or more syringes for use with the detection of a target species.

Other kits according to the present invention include at least one rubbed substrate and a liquid crystal. These kits may also be used to detect the presence of a target species in a sample. The method includes contacting a portion of the rubbed substrate of the kit with a quantity of the sample; placing the liquid crystal of the kit on the portion of the rubbed substrate structure that had contacted the sample; and determining whether the uniform anchoring of the liquid crystal has been disrupted. If the uniform anchoring of the liquid crystal has been disrupted, then the target species is present in the sample. Determining whether the uniform anchoring of the liquid crystal has been disrupted may be accomplished by various methods. One such method includes viewing the rubbed substrate through cross polarizers.

A method for detecting the presence of a target species using a liquid crystal assay device such as that described above includes several steps. First, a rubbed substrate structure is incubated with a sample to be tested for the presence of a target species. Typically, the incubation period will be around 2 hours, but this may be varied depending on the particular target species and the biomolecule recognition agent capable of specifically recognizing and binding the target species. Second, a spacing material such as a film is placed between the incubated rubbed substrate structure and the surface that uniformly anchors liquid crystals such that the biochemical blocking layer side of the rubbed substrate structure faces the surface that uniformly anchors liquid crystals. Third, a liquid crystal such as 5CB is drawn into the area between the incubated rubbed substrate structure and the surface that uniformly anchors liquid crystals. Typically, the liquid crystal is in an isotropic phase during this step. The liquid crystal may need to be heated prior to drawing it into the area between the incubated rubbed substrate structure and the surface that uniformly anchors the liquid crystal. The liquid crystal can also be drawn into the cell in the nematic phase. Finally, the person conducting the assay determines whether the liquid crystal is uniformly anchored on the rubbed substrate structure. If the liquid crystals are uniformly anchored on the rubbed substrate structure, the sample will be found to not contain the target species. On the other hand, if the liquid crystal is not uniformly anchored on the rubbed substrate structure, then the sample will be found to contain the target species.

In addition to the method described above, kits and assay devices to be used in accordance with the present invention may also be designed such that the sample to be tested is passed directly through or maintained in a preassembled cell including the rubbed substrate structure, the spacing material, and the surface that uniformly anchors the liquid crystals. Once a sufficient time has passed, the sample may be removed followed by addition of liquid crystal to determine whether or not the target species was present in the sample.

In addition to the methods described above, kits and assay devices to be used in accordance with the present invention may also be designed such that liquid crystal is placed directly onto the surface of an incubated rubbed substrate structure and the orientation of the liquid crystal is observed with one surface of the liquid crystal on the rubbed substrate being a surface with air. That is, the liquid crystal is simply placed onto the surface. It is well known that the orientation of 5CB, for example, is homeotropic at the liquid-crystal air interface. Thus, the free surface of the liquid crystal can substitute for the second surface that uniformly anchors the liquid crystal. This type of kit is particularly useful for microarrays of patterned recognition groups.

EXAMPLES

The following materials and methodologies were utilized in the examples discussed in greater detail below.

Materials

Glass microscope slides used in the experiments were marked premium grade and obtained from Fisher Scientific (Pittsburgh, Pa.), and polished silicon (100) wafers were obtained from Silicon Sense (Nashua, N.H.). Glass slides and silicon wafers were cleaned prior to use by treating with "piranha solution" (70% $H_2SO_4$/30% $H_2O_2$). "Piranha solution" should be handled with extreme caution because it reacts violently with organic materials and should not be stored in closed containers. After cleaning for 1 hr at 80° C. in "piranha solution", the slides and silicon wafers were rinsed copiously in deionized water, and dried under a stream of nitrogen. Prior to use, the clean substrates were stored in an oven heated at 120° C. for at least 3 hrs.

Various chemicals were used in the experiments. Octadecyltrichlorosilane (OTS) and 3-Amiopropyltriethoxysilane (APES) were both purchased from Gelest (Tullytown, Pa.). Solutions for silylating the glass microscope slides using OTS were prepared using anhydrous toluene (Aldrich, Milwaukee, Wis.) as solvent whereas solutions for silylating the glass microscope slides using APES were prepared using 10 mM sodium acetate-acetic acid buffered (pH 5.0) solution. Disuccinimidyl suberate (DSS) was obtained from Pierce (Rockford, Ill.). Solutions of DSS were prepared using anhydrous methanol and dimethyl sulfoxide (DMSO) which were obtained from Aldrich (Milwaukee, Wis.). Bovine serum albumin (BSA, IgG free, lyophilized powder), anti-BSA (developed in rabbit), anti-streptavidin (developed in rabbit), anti-FITC (monoclonal, clone FL-D6, mouse ascites fluid), fibrinogen (fraction I, type III from human plasma), lysozyme (EC 3.2.1.17, grade III: from chicken egg white), and anti-biotin IgG (polyclonal, developed in goat) were obtained from Sigma (St. Louis, Mo.) and used as received. Biotinylated bovine serum albumin (biotin-BSA, mole of biotin/mole of BSA=8) was obtained from Pierce (Rockford, Ill.). All proteins used in the studies were dissolved in phosphate-buffered saline (PBS) buffer solution at pH 7.2. All aqueous solutions were prepared using Milli-$Q^{plus}$ brand deionized water (18.2 M$\Omega$.cm) obtained from Millipore (Bedford, Mass.). Buffer solutions were prepared using analytical grade reagents. The nematic liquid crystal, 4-cyano-4'-pentylbiphenyl (5CB), manufactured by BDH was purchased from EM industries (Hawthorne, N.Y.).

Preparation of Substrates with Physically Adsorbed Layers of BSA

Hydrophobic and hydrophilic substrates were prepared for studies of the physical adsorption of BSA onto these surfaces. Clean glass slides and silicon wafers were used as the hydrophilic substrates. The hydrophobic substrates were prepared by overnight treatment of the glass slides and silicon wafers with an OTS solution (3% OTS in anhydrous toluene). To eliminate the potential for hydrolysis, the silylation with OTS was conducted under nitrogen in a glove box (model CC-40, Vacuum Atmospheres Co., Hawthorne, Calif.). The substrates silylated with OTS were rinsed with toluene and dried at 120° C. for at least 3 hrs prior to further use. BSA was physically adsorbed onto the hydrophilic and hydrophobic substrates by immersing them overnight in a 1 mg/mL BSA solution in PBS buffer (pH 7.2).

Preparation of Substrates with Chemically Immobilized Layer of BSA

Substrates with chemically immobilized layers of BSA were prepared using the experimental procedure schematically shown in FIG. 1. The clean glass slides were aminopropylated by reaction for 3 hrs at 80° C. with 10% APES in a sodium acetate-acetic acid buffer solution (10 mM, pH 5.0). The aminopropylated substrates were rinsed with deionized water and then dried at 120° C. for at least 3 hours before they were activated with a succinimide ester cross-linker (DSS) to promote the coupling of the BSA to the surface by amide bond formation. The aminopropylated substrate was immersed in anhydrous methanol and then a 50 mM DSS stock solution in anhydrous DMSO was added in a quantity sufficient to produce a 1 mM DSS solution. The mixture was stirred for 1 hr, washed with methanol, and immediately coupled to an amine group on BSA. The BSA coupling was achieved by overnight immersion of the DSS-activated glass slide in a 1 mg/mL BSA solution in PBS buffer (pH 7.2).

Preparation of Substrates with Rubbed Films of BSA

Rubbed BSA films were prepared by sliding rubbing material across BSA-immobilized glass slides using a strip chart recorder (Model No. SR-255 A/B, Heath Company) that was modified for rubbing as shown in FIG. 2. A velvet-type polyester cloth (90% polyester/10% spandex) obtained from Logantex Inc. (New York, N.Y.) was used as the rubbing material in this study. The rubbing material was attached on the top of the moving guide (chart paper) using double-sided tape, and the BSA-immobilized glass slide was placed on the rubbing material. Because the glass slide could be fixed in place, rubbing was achieved by movement of the rubbing material guided by chart paper. The rubbing time was 1 min using a 5 mm/sec speed on the chart recorder. The applied pressure was about $10^3$ Pa, and it was obtained by loading a weight (an aluminum block of ~200 g with dimensions of about 1 inch by 3 inches) onto the glass slide.

Preparation of Substrates with Chemically Immobilized Layer of Biotin-BSA

Substrates with chemically immobilized layers of biotin-BSA were prepared using the experimental procedure schematically shown in FIG. 1 using biotinylated BSA in place of BSA. The clean glass slides were aminopropylated by reaction for 3 hrs at 80° C. with 5% APES in a sodium acetate-acetic acid buffer solution (10 mM, pH 5.0). The aminopropylated substrates were cleaned three times with sodium acetate-acetic acid buffer in a sonication bath for 10 minutes at 80° C., rinsed with deionized water, and then dried at 120° C. for at least 3 hours before they were activated with a succinimide ester cross-linker (DSS) to promote the coupling of the biotin-BSA to the surface by amide bond formation. The aminopropylated substrate was immersed in anhydrous methanol and then a 50 mM DSS stock solution in anhydrous DMSO was added in a quantity sufficient to produce a 1 mM DSS solution. The substrate was immersed in the stirred mixture for 1 hr, washed with methanol and deionized water, and then immediately coupled to an amine group on biotin-BSA. The biotin-BSA coupling was achieved by immersing the DSS-activated glass slide in a 1 mg/mL biotin-BSA solution in PBS buffer (pH 7.2).

Preparation of Substrates with Rubbed Films of Biotin-BSA

Rubbed films of biotin-BSA were prepared by sliding a velvet-type cloth (90% polyester/10% spandex) obtained from Logantex Inc. (New York, N.Y.) across the biotin-BSA coated substrate prepared as described above. The rubbing was accomplished using a strip chart recorder (model SR-255 A/B Heath Company) that was modified for rubbing as shown in FIG. 2. The cloth was attached on the top of the moving guide (chart paper) using double-sided tape, and the (biotin-BSA)-immobilized glass slide was placed face down on the cloth. Because the glass slide could be fixed in place, rubbing was achieved by movement of the rubbing material guided by chart paper. The rubbing speed and length were controlled by changing the feeding speed of the chart recorder and the rubbing time respectively. Rubbing pressure was controlled by placing an aluminum block of different mass onto the substrate prior to rubbing. As a standard condition, a rubbing speed of approximately 2.1 mm/second (5 inches/minute), a rubbing length of approximately 127 mm (rubbing time of 1 minute), and a rubbing pressure of approximately 1,000 Pa (an aluminum block with a mass of approximately 200 grams and dimensions of 2.54 cm by 7.62 cm) were used.

General Preparation of Rubbed BSA Film with Biomolecule Recognition Agent

Substrates with chemically immobilized layers of BSA and a chemically immobilized biomolecule recognition agent are prepared using the experimental procedure schematically shown in FIG. 1 except that the biomolecule recognition agent, an immunoglobulin or fragment thereof, is reacted with the DSS prior to treating the modified activated surface with BSA. Clean glass slides are aminopropylated by reaction for 3 hrs at 80° C. with 10% APES in a sodium acetate-acetic acid buffer solution (10 mM, pH 5.0). The aminopropylated substrates are then rinsed with deionized water and dried at 120° C. for at least 3 hours before they are activated with a succinimide ester crosslinker (DSS) to promote the coupling of the immunoglobulin or immunoglobulin fragment and BSA to the surface by amide bond formation. The aminopropylated substrate is immersed in anhydrous methanol and then a 50 mM DSS stock solution in anhydrous DMSO is added in a quantity sufficient to produce a 1 mM DSS solution. The mixture is stirred for 1 hr, washed with methanol, and immediately coupled to an amine group on an immunoglobulin or fragment of an immunoglobulin. The immunoglobulin or fragment thereof is achieved by overnight immersion of the DSS-activated glass slide in a 100 ng/mL PBS buffered solution of the immunoglobulin or fragment thereof. The slide is then rinsed with deionized water and treated with BSA to produce the final substrate surface ready for rubbing. The BSA coupling is achieved by overnight immersion of the glass slide in a 1 mg/mL BSA solution in PBS buffer (pH 7.2). The surface of the substrate containing the immobilized BSA and immunoglobulin or fragment thereof is then rubbed according to the procedures outlined above.

Rubbed Substrates without BSA Layer

Rubbed glass slides without a BSA layer and glass slides with a shear-deposited Teflon film on them were prepared for preliminary studies of protein adsorption on rubbed films. Rubbed glass slides without a BSA layer were prepared by mechanically rubbing the non-BSA containing glass slide under the same conditions described above with respect to slides containing BSA. Glass slides with a shear-deposited Teflon film on them were obtained by sliding a flat Teflon block across fused glass slides in a motorized machine. A temperature of approximately 100° C. was used in shear-depositing the Teflon on the glass slides, as this gave more complete and reproducible surface coverage than was achieved when lower temperatures were used. The applied pressure and speed were also controlled, and were respectively about $10^3$ Pa and 0.5 mm/s for 15 sec.

Protein Adsorption

To study protein adsorption by a variety of biochemicals, rubbed films of chemically-immobilized BSA were incubated with various protein solutions in PBS buffer (pH 7.2) for 2 hrs. Such solutions included a 100 nM polyclonal anti-BSA IgG solution for specific binding; a 10 mg/mL BSA solution to study additional adsorption of BSA; a 100 nM anti-FITC IgG solution; a 0.2 mg/mL fibrinogen solution; and a 0.2 mg/mL lysozyme solution. The anti-FITC, fibrinogen, and lysozyme solutions were prepared to investigate non-specific adsorption by the chemically-immobilized BSA substrate.

Binding of Anti-Biotin IgG by Rubbed Films of Biotin-BSA

Rubbed films of biotin-BSA prepared as described above were incubated in PBS solutions of anti-biotin IgG at different concentrations at pH 7.2 for 90 minutes. During incubation, the solution of IgG was stirred using a magnetic stir bar. After removal from the protein solutions, the substrates were rinsed with deionized water and dried under a stream of dry nitrogen.

Optical Cells

Optical cells were prepared by pairing two glass slides and by spacing one side of them apart using ~10 µm thick films of Mylar® brand film obtained from Dupont Films (Wilmington, Del.). The rubbed films were aligned so that they faced each other such that the rubbing directions of the films were parallel within the cell. The cells were held together using "bulldog" clips placed along the edge of the glass microscope slides. The cell was placed on the hot plate at 40° C. and heated with hot air for approximately 10 sec. The nematic liquid crystal of 5CB was heated into its isotropic phase (~35° C.) in a glass syringe. A drop of 5CB was then placed on the edge of each cell on the hot plate. The 5CB was then drawn into the optical cells by capillary action. Once the optical cells were filled with 5CB, the cell was removed from the hot plate and cooled in air to room temperature. Upon cooling, the isotropic phase of 5CB transformed to the nematic phase.

Polarized Light Microscopy

A polarized light microscope (BX60, Olympus, Tokyo, Japan) was used to observe the optical textures formed by light transmitted through the optical cells filled with 5CB. All images except those using the rubbed biotin-BSA substrates were obtained using a 20×objective lens with a 550 µm field of view between cross-polars. A 10×objective lens with a 1.0 mm filed of view between crossed polarizers was used to obtain images of the cells constructed from the rubbed biotin-BSA substrates. Images of the optical appearance of liquid crystal optical cells prepared from the rubbed biotin-BSA substrates were captured with a digital camera (C-2020 Z, obtained from Olympus America Inc. (Melville, N.Y.)) that was attached to the polarized light microscope. The pictures of the optical cells prepared using the rubbed biotin-BSA substrates were obtained using high quality mode (resolution of 1600×1200 pixels) at an aperture of f11 and shutter speed of $\frac{1}{160}$ seconds. The analysis of the optical textures of cells made from the rubbed biotin-BSA substrates was made using Photoshop software (Adobe Systems Incorporated, San Jose, Calif.) to calculate the average luminance (average pixel value on a scale of 0–255) of the image after conversion of the image from color to gray scale. The azimuthal orientation of liquid crystal for all optical cells was determined by the change in interference colors upon insertion of a quarter-wave plate (Normarski prism, 147.3 nm) into optical path. All optical cells were placed in the microscope with the rubbing direction parallel to the slow axis of a quarter-wave plate corresponding to 45° rotation of the optical cell with respect to the axis of the polarizer. The slow axis was determined by observing the direction of the interference shift. That is, the interference color shifted toward higher retardation in Michel-Lévy chart when the slow axis of the liquid crystal and the quarter-wave plate coincided.

Transmittance of Optical Cells

The intensity of light transmitted through each optical cell was recorded during rotation of the sample between cross-polars. The background intensity ($I_{Background}$) of light transmitted through cross-polars and the maximum intensity ($I_{Parallel}$) of light transmitted through parallel polars were recorded for an empty optical cell (without filling the 5CB). The intensity values reported were corrected for the background intensity of light passed through cross-polars and are normalized by the intensity of light measured to pass between parallel polars (both empty cells). That is, corrected and normalized, the fractional transmittance is given by the following equation:

$$\text{Fractional Transmittannce} = \frac{I - I_{Background}}{I_{Parallel}} \quad (1)$$

All intensities of light transmitted were measured by a silicon photodiode (silicon photodiode FDS100, Thorlabs, Inc., Newton, N.J.).

Ellipsometric Thickness

For ellipsometric measurements, silicon wafers were used as the substrate instead of glass slides. The sample substrates for measurement were prepared using the same procedure used to prepare the glass slides for optical measurement. Ellipsometric thickness was measured at three points on each sample using a Rudolph Auto EL ellipsometer (Flanders, N.J.) at a wavelength of 6320 Å and an angle of incidence of 70°. In order to interpret the ellipsometric thickness of bound protein, a simple two layer model (organic layer/effective substrate of $SiO_2$/Si) was used. To perform the calculations, a refractive index of 1.46 was used for the organic films formed on the silicon wafers.

Out-of-Plane Orientations of 5CB

A home-built optical apparatus was used to measure the out-of-plane orientation (tilt angle) of 5CB within the optical cells. The apparatus included a 10 m W He—Ne laser, a polarizer, a computer controlled stage that permitted rotation of the sample, an analyzer, and a photodiode. The optical cells were placed between cross-polars, illuminated at normal incidence using a polarized He—Ne laser, and then rotated from −20° to +20° with respect to the normal. A plot of the intensity of light transmitted through the cell against the angle of incidence was used to estimate the tilt of the optical axis of the liquid crystal from the surface of the cell.

DISCUSSION OF EXPERIMENTAL RESULTS

Stability of Biochemical Blocking Layers to Rubbing

Figure 3:
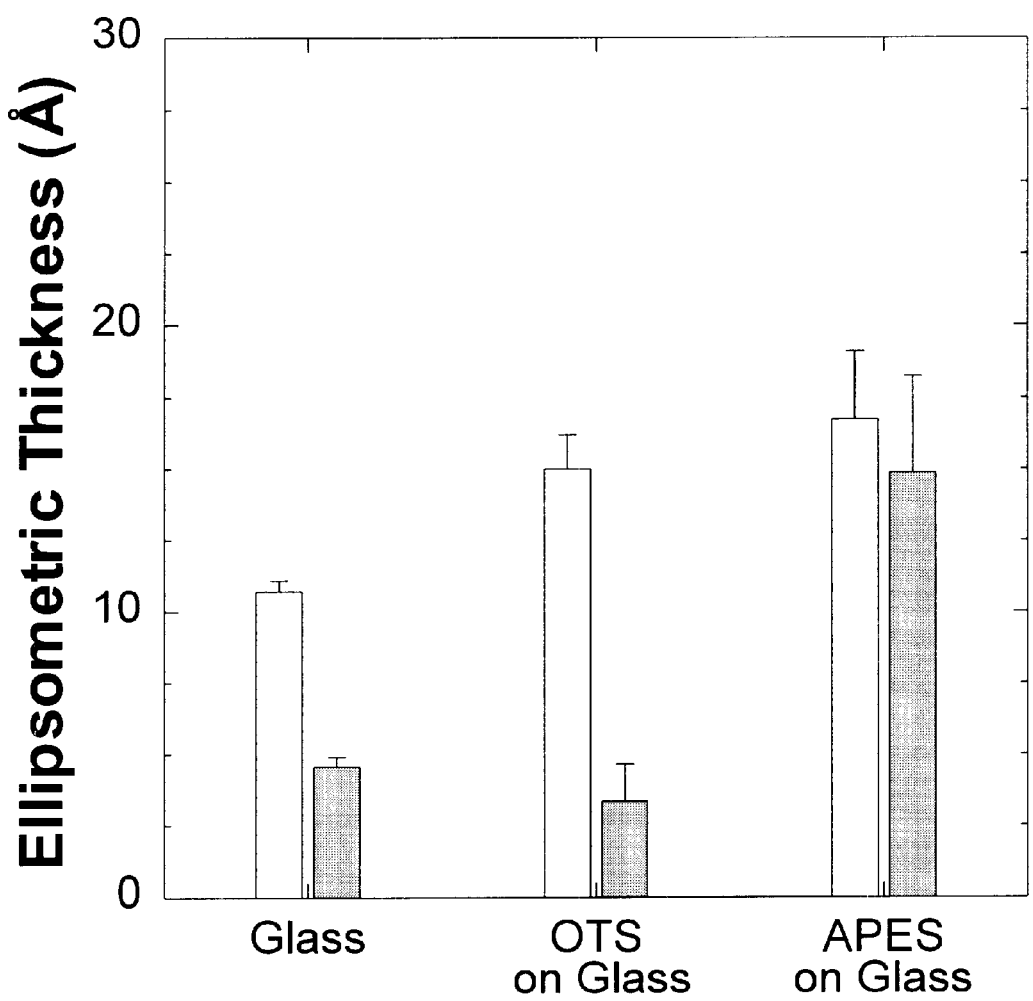
FIG. 3 is a bar graph showing ellipsometric thickness of BSA layers on glass slides before (no shading) and after rubbing (shaded) using the apparatus shown in FIG. 2. The BSA layers were physically adsorbed on clean, untreated glass slides and on OTS-treated glass slides. BSA was chemically immobilized on glass slides which had been modified by reaction with APES followed by reaction with DSS as shown in FIG. 1. The rubbed films of BSA were prepared with an applied pressure of $10^3$ Pa for one minute at a speed of 5 mm/sec. The bar graph shows that significantly less BSA layer is lost when the glass slide with the chemically immobilized BSA is rubbed as compared to the BSA layers on the other slides.

As noted above, a biochemical blocking compound such as BSA is preferably covalently immobilized on a support although this is not required. In order to investigate the stability of a substrate structure with a non-immobilized biochemical blocking layer, substrate structures were prepared using clean glass slides and hydrophobic slides which were modified by reaction with OTS. BSA was then physically adsorbed onto the surface of the slides followed by rubbing using the apparatus shown in FIG. 2. As shown in FIG. 3, measurements of ellipsometric thickness indicated that over 50% of the physically adsorbed BSA was lost upon rubbing regardless of whether the support was the clean glass slide or the slide treated with OTS. On the other hand, as shown in FIG. 3, little change in ellipsometric thickness was observed when a substrate structure prepared according to the scheme shown in FIG. 1 was rubbed. Thus, immobilization of the biochemical blocking layer using the method shown in FIG. 1 has been shown to overcome the loss in thickness due to rubbing of the biochemical blocking layer.

Orientation of Liquid Crystals on Rubbed Films of Immobilized BSA

The optical texture of various optical cells was investigated to determine the effect that rubbing has upon the anchoring of liquid crystals drawn into the optical cell. Specifically, the optical textures between cross-polars of 5CB sandwiched between glass slide supports containing immobilized BSA prepared as shown in FIG. 1 were observed and photographically recorded. Before rubbing, the optical texture of 5CB in contact with the BSA-immobilized layer was non-uniform. Rubbing of the BSA-immobilized layer produced uniform alignment of 5CB when it was drawn into an optical cell prepared using the rubbed substrate structure. The azimuthal orientation of the liquid crystal in the rubbed BSA layer was easily determined by the change in interference colors upon insertion of a quarter-wave plate into optical path (See details in Experimental Section). The interference colors after insertion of the quarter-wave plate shifted the colors toward a higher retardation, which indicated that the alignment of the liquid crystals was parallel to the rubbing direction.

The out-of-plane orientation (tilt angle) of 5CB supported on surfaces was also determined using the same cell utilized in the above analysis. By mounting the cells in the crystal rotation apparatus (See details in Experimental Section), the tilt angle of the optical axis of 5CB from the plane containing the rubbed BSA layer was determined to be 1.5±0.5°. Therefore, these measurements show that rubbing films of immobilized BSA induces 'planar' and 'parallel' orientation of 5CB with respect to the rubbing direction.

Uniformity Analysis of Liquid Crystal Using Light Transmittance

Figure 4:
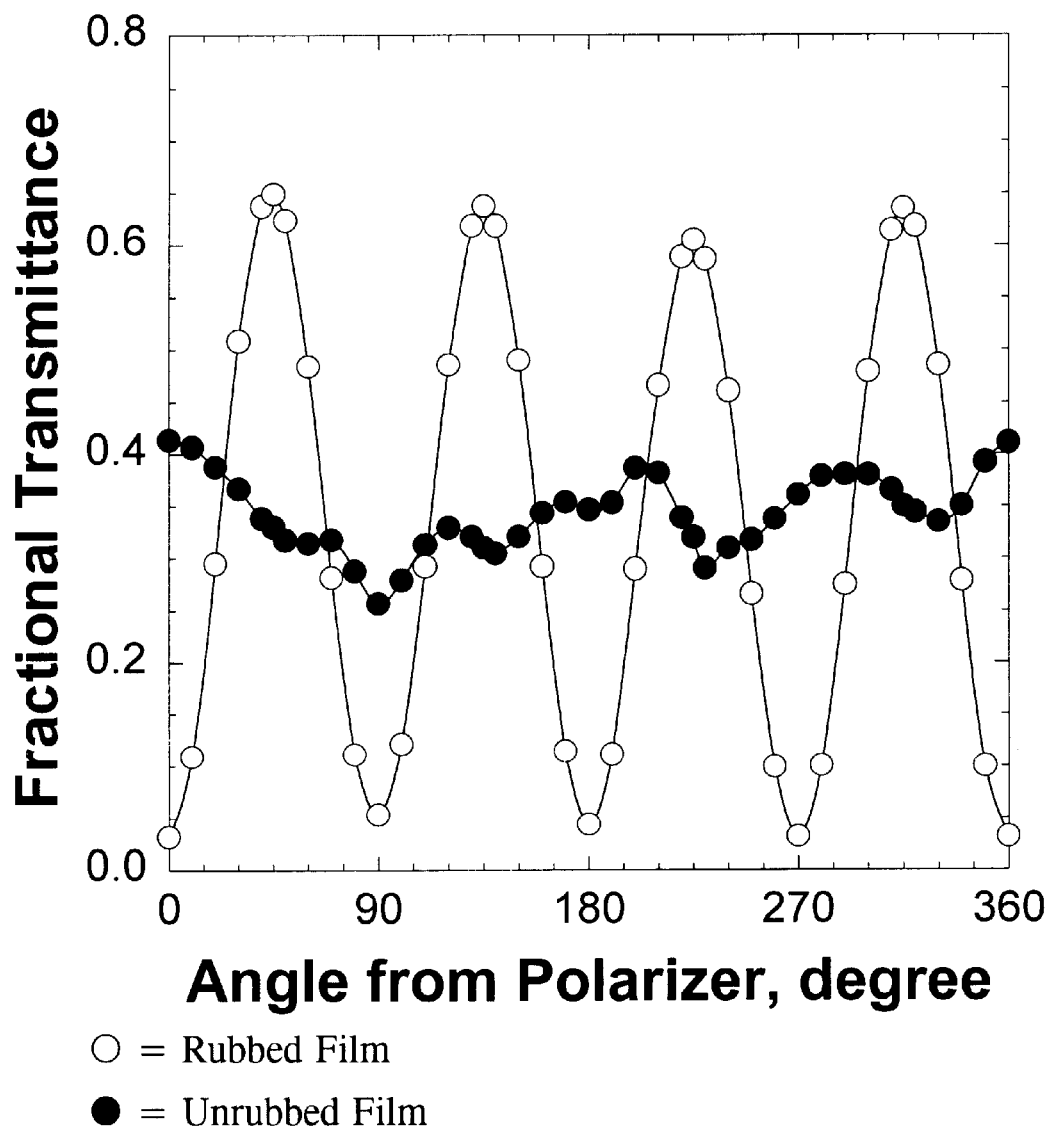
FIG. 4 is a graph showing the fractional transmittance of light between cross-polars and 5CB anchored on rubbed (○) and unrubbed (●) glass slides containing chemically-immobilized BSA prepared according to FIG. 1. The fractional transmittance is shown as a function of the angle between the sample and the polarizer. The fractional transmittance is the ratio of the intensity of light transmitted through the optical cell containing the liquid crystal and between the cross-polars to the maximum intensity of light transmitted through an empty cell under parallel-polars.

The light extinction between dark and bright images which occurred when the optical cell was rotated is caused by light transmitted through an optical cell between cross-polars. The dark image that is observed when the rubbing direction is parallel to the polarizer or analyzer indicates that the liquid crystals have a uniform alignment. The intensity of light transmitted through each optical cell was recorded when the sample was rotated between cross-polars. This technique was used to characterize the uniformity of the anchoring of liquid crystals on the rubbed film of immobilized BSA (○ in FIG. 4). The strong modulation in the intensity of light transmitted through cross-polars during rotation of the cell with respect to the polarizer as reflected in the fractional transmittance measurement (See details in Experimental Section), indicated the uniform anchoring of liquid crystals in the rubbed immobilized BSA substrate structure. On the other hand, for the unrubbed immobilized BSA substrate (● in FIG. 4), which exhibited non-uniform anchoring of liquid crystals, the intensity of transmitted light was independent of the angle of rotation of the sample. This is further confirmation that the strong modulation in light transmittance measured during rotation of the optical cell prepared from the rubbed immobilized BSA substrate structure between cross-polars results from the uniform anchoring of 5CB on the rubbed film of immobilized BSA.

Anisotropy in Rubbed Films and Effects of Protein Adsorption

As described above, rubbed films of immobilized BSA uniformly align 5CB when the liquid crystal contacts the rubbed substrate structure. Experiments were conducted to determine whether the binding of proteins erased the anisotropic property in the alignment layer. For this purpose, rubbed films having no BSA layer were prepared. This was accomplished by rubbing glass slides that did not have any biochemical blocking compound on them and by using glass slides that had shear-deposited Teflon film on them. Glass slides with shear-deposited film on them are known to induce uniform alignment of liquid crystal. Dennis, J. R.; Vogel, V. J. *J. App. Phys.* 83 (1998) p. 5195. Because BSA easily adsorbs on most surfaces, it was expected that the BSA would completely cover the rubbed surfaces by physical adsorption. It was observed that liquid crystals on the rubbed glass slide and the shear-deposited Teflon film align uniformly on the surface prior to immersion in a solution of BSA. However, after immersion in a 0.1 mg/ml BSA solution, nematic phases of 5CB supported on rubbed glass slide and shear-deposited Teflon layer do not extinguish light transmitted through the cell at any angle of the sample relative to the polarizer. In other words, the textures are completely non-uniform, and there are no preferred directions of azimuthal anchoring. Thus, the change in the morphology caused by the adsorption of BSA on the rubbed glass slide and the shear-deposited Teflon film disrupted the anisotropy of the surface and resulted in non-uniform anchoring of the liquid crystal. Thus, the adsorption of BSA on the rubbed glass slide and the shear-deposited Teflon film disrupted the anisotropy of the surface and resulted in non-uniform anchoring of the liquid crystal. Therefore, it can be concluded that an alignment or biochemical blocking layer having selectivity in protein adsorption should be suitable as a substrate structure for use in a liquid crystal assay device. These results also show that because clean glass or Teflon films do not resist non-specific adsorption of proteins, a biochemical blocking layer which resists non-specific protein adsorption is necessary in a liquid crystal assay device.

Non-specific Adsorption of Proteins in BSA Layer

Figure 5:
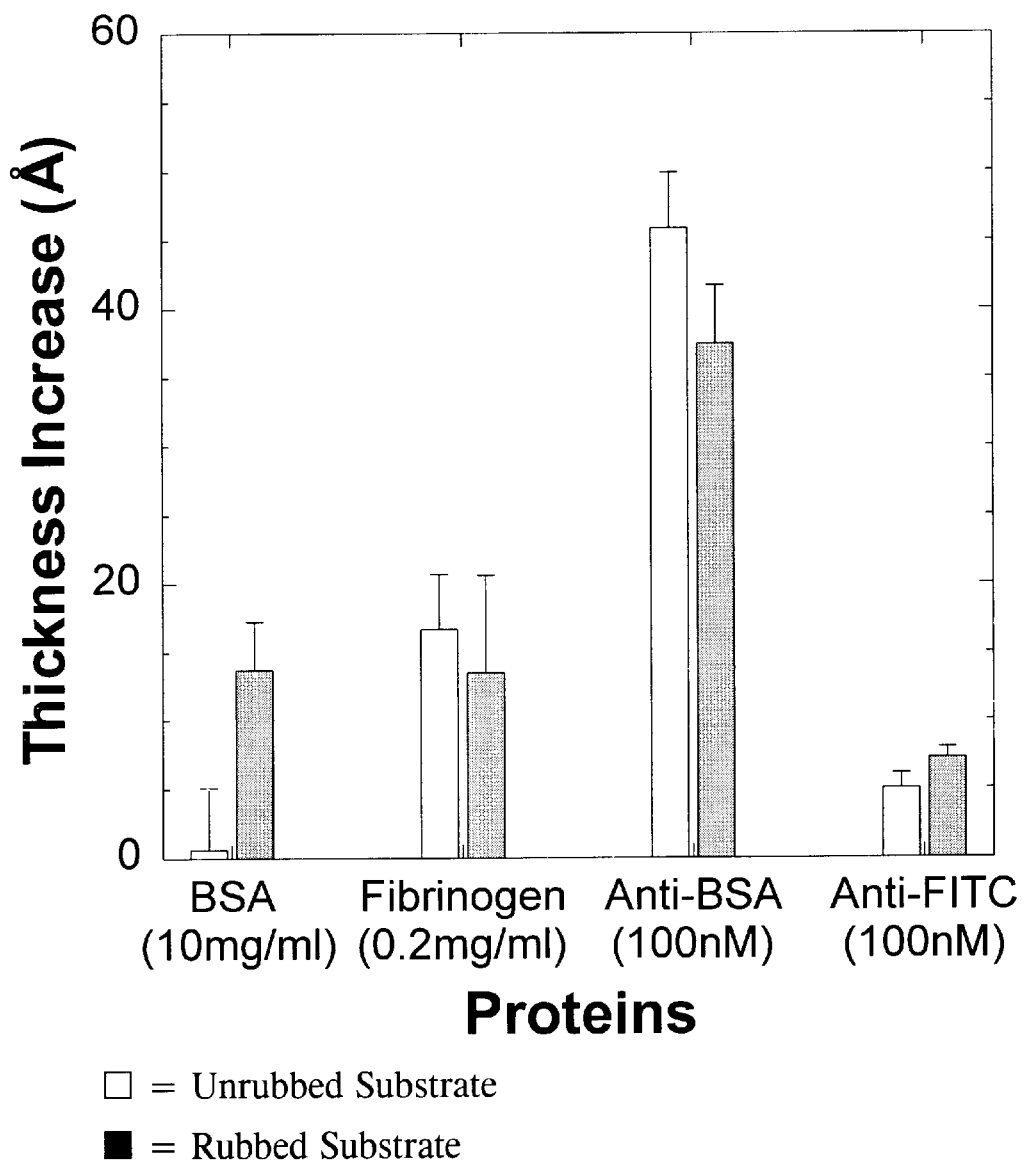
FIG. 5 is a bar graph showing the increases in ellipsometric thickness of rubbed (shaded) and unrubbed (not shaded) silicon wafers with BSA chemically immobilized on the surface after immersion in various solutions. The increase in ellipsometric thicknesses of the BSA-immobilized substrates was determined after two hour immersion in PBS-buffered solutions of 10 mg/mL BSA; 0.2 mg/mL fibrinogen; 100 nM anti-BSA; and 100 nM anti-FITC. The Figure shows the significant increase in thickness which occurs when the BSA-immobilized substrate is immersed in the anti-BSA PBS-buffered solution.

As described above, a biochemical blocking layer should effectively resist non-specific adsorption of protein if it is to be effective. The optical texture of a liquid crystal supported on a rubbed film of immobilized BSA after immersion of the rubbed film in an aqueous solution containing 10 mg/ml of BSA was observed and photographically reported. When compared with the appearance of the liquid crystal on the rubbed film of BSA without immersion, the optical appearance of the liquid crystal is changed little by immersion of the rubbed film of BSA in the solution of BSA. This result contrasts to the optical appearance of the liquid crystal on the rubbed films of Teflon and glass following immersion in the aqueous solution of BSA. The ellipsometric thickness of films of BSA was measured with and without rubbing after immersion in the solution of BSA (FIG. 5). Inspection of FIG. 5 reveals that a covalently immobilized film of BSA (not rubbed) does not adsorb a measurable amount of BSA when immersed and withdrawn from an aqueous solution containing BSA. In contrast, when rubbed, the covalently immobilized layer of BSA does adsorb approximately 15 Å of BSA. Therefore, it was concluded that the level of non-specific adsorption of BSA is greater on the rubbed film of BSA as compared to the film of BSA that was not rubbed. The level of non-specific adsorption of BSA on the rubbed film, however, was insufficient to disrupt the uniform anchoring of the liquid crystal. As shown below, this result contrasts with the effects of specific binding of anti-BSA IgG on rubbed films of BSA. In this case, specific binding of anti-BSA IgG was observed to trigger the non-uniform anchoring of liquid crystal on the rubbed film of BSA.

The optical appearance of 5CB anchored on a rubbed film of BSA that was immersed and withdrawn from aqueous solutions containing fibrinogen and lysozyme was also investigated. Whereas immersion of the rubbed film of BSA into lysozyme resulted in a uniform orientation of the liquid crystal as observed and photographically recorded, a number of defects (loop disclinations) appeared in the optical texture of liquid crystal supported on the film of rubbed BSA immersed into fibrinogen. Although defects were evident in the optical appearance of the liquid crystal supported on the film of rubbed BSA immersed into fibrinogen, it should be noted that the bulk of the liquid crystal remained uniformly oriented. As shown below, the level of uniformity (by measurement of fractional transmittance) was quantified and shows that it is clearly distinguishable from the appearance of liquid crystal in cases where specific binding of anti-BSA IgG to the rubbed film takes place. Whereas the optical appearance of the liquid crystal after immersion of the rubbed films in aqueous solutions of BSA and fibrinogen differed from one another because of the small defects in the optical texture of the liquid crystal supported on the rubbed film after immersion in fibrinogen, the ellipsometric thickness measurements of non-specifically adsorbed BSA and fibrinogen reveal very similar levels of adsorption (FIG. 5). This result demonstrates that the liquid crystal can distinguish between adsorbed protein layers that are indistinguishable when characterized by ellipsometric methods. The non-specific adsorption of fibrinogen (approximately 15 Å) was additionally measured on films of immobilized BSA, and it was found to be independent of whether or not the film was rubbed.

The tilt angles of the liquid crystal were also measured after non-specific adsorption of BSA and fibrinogen on the rubbed films of BSA. The measured tilt angles were 3.8±0.8° and 3.5±0.5° for BSA and fibrinogen, respectively. As described above, the tilt of the liquid crystal was 1.5°±0.5 prior to immersion of the rubbed films of BSA into aqueous solutions of BSA or fibrinogen. This result suggests that non-specific adsorption gives rise to a small change (2 degrees or less) in the tilt of the liquid crystal. Therefore, it was concluded that the rubbed films of immobilized BSA resist the non-specific adsorption of proteins at levels that largely sustain a uniform planar orientation of 5CB in a direction that is parallel to the direction of rubbing of the BSA.

Specific Binding of Proteins in Rubbed BSA Layer

To be suitable for use in a liquid crystal assay device, a blocking layer should possess an anisotropic structure that is erased by specific binding to a target species to be detected in a sample. Rubbed films of immobilized BSA were immersed into various PBS-buffered 100 nM antibody for 2 hrs. After immersion in a solution of anti-BSA, the texture of an optical cell containing rubbed immobilized BSA had an almost non-uniform texture. Thus, binding of the anti-BSA by the BSA blocking layer on the rubbed substrate structure erased the anisotropy of the rubbed surface. In contrast, immersion of the rubbed immobilized BSA substrate structure in solutions of antibodies such as anti-FITC and anti-streptavidin did not change the uniform textures at all similar to the results obtained when the rubbed substrate was placed in the aqueous solution of BSA. As shown in FIG. 5, ellipsometric thickness measurements clearly indicated specific binding by anti-BSA and the change to non-uniform texture caused by specific binding. Compared with immersion in BSA, fibrinogen, and anti-FITC solutions, the specific binding resulting from immersion in the anti-BSA solution gave a large increase (40 Å or more) in the thickness. This is true even though the optical cells resulting from immersion in BSA and fibrinogen used substantially higher concentrations of protein. Additionally, because the thickness increase is independent of rubbing, it was deduced that the binding sites of BSA for the antigen-antibody reaction were not damaged by rubbing. Therefore, it was discovered that rubbed films of BSA resist non-specific adsorption and offer a surface in which anisotropy is erased by specific binding.

Transmittance Analysis for Specific and Non-Specific Adsorption

Figure 6:
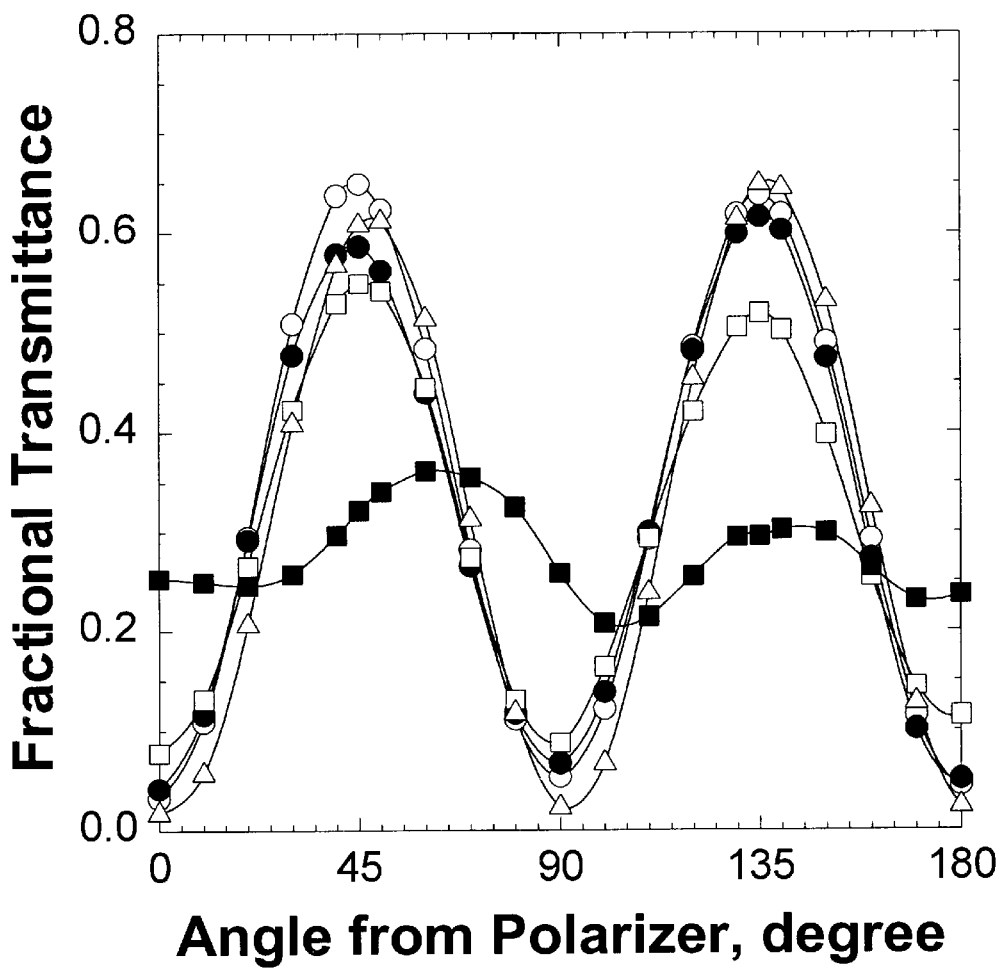
FIG. 6 is a graph showing the fractional transmittance of light between cross-polars and 5CB anchored on rubbed films of BSA after immersion into protein solutions as a function of the angle between the rubbing direction of cell and polarizer. As a reference, fractional transmittance for the rubbed films of immobilized BSA was measured (○) without immersion in any further solution. For non-specific adsorption by proteins, rubbed films of immobilized BSA were incubated for 2 hours in PBS-buffered solutions of 10 mg/mL BSA (●) and 0.2 mg/mL fibrinogen (□). For specific binding by antibodies, rubbed films of immobilized BSA were incubated for 2 hours in PBS-buffered solutions of 100 nM anti-BSA (■) and 100 nM anti-FITC (△).

A transmittance analysis of the rubbed immobilized BSA substrate structures after immersion in the various solutions described above was performed to obtain a quantitative comparison between specific and non-specific binding by the rubbed substrate structure. FIG. 6 shows that specific binding with anti-BSA erases not only the extinction by rotating the cell, but also the periodical transmittance property of the rubbed BSA layer. Table 2 summarizes the fractional intensities of maximum ($I_{Max}$) and minimum ($I_{Min}$) values for each protein adsorption through immersion experiment and normalizes the difference of extinction between maximum and minimum transmittance ($[I_{Max}-I_{Min}]/I_{Max}$), which is more useful for comparison between specific and non-specific adsorption. It was determined that $[I_{Max}-I_{Min}]/I_{Max}$ for the specific binding with anti-BSA was about 0.33. Thus, a dramatic decrease occurs upon specific binding. This is especially true considering that the value of $[I_{Max}-I_{Min}]/I_{Max}$ for rubbed films of immobilized BSA is about 0.94. Even in the case of non-specific adsorption, the values of normalized fractional transmittance are over 0.90 except for with fibrinogen. Even though $[I_{Max}-I_{Min}]/I_{Max}$ for the fibrinogen adsorption is relatively low (~0.84) compared with other non-specific adsorption, its value is much closer to that of non-specific adsorption rather than that of specific adsorption such as with the anti-BSA. Also, as shown in FIG. 6, the periodic property in the light transmittance of the rubbed immobilized BSA substrate surface immersed in fibrinogen obviously continues and is clearly different from light transmittance from the specific binding resulting from immersion in the anti-BSA solution. Therefore, in addition to observations by optical textures and ellipsometric thickness, results obtained from transmittance measurements indicate that rubbed immobilized BSA substrate structures orient liquid crystals uniformly, resist non-specific adsorption, and possess anisotropic structure that can be erased by specific binding.

TABLE 2

Fractional Transmittance of Liquid Crystal Cells by Protein Adsorption[a]

| Protein (concentration) | fractional transmittance $I_{Max}$[b] | $I_{Min}$[c] | $\frac{I_{max} - I_{min}^d}{I_{Max}}$ |
|---|---|---|---|
| reference[e] | 0.63 ± 0.02 | 0.03 ± 0.01 | 0.94 ± 0.01 |
| BSA (10 mg/ml) | 0.61 ± 0.02 | 0.05 ± 0.01 | 0.91 ± 0.02 |
| Fibrinogen (0.2 mg/ml) | 0.58 ± 0.05 | 0.09 ± 0.02 | 0.84 ± 0.02 |
| Lysozyme (0.2 mg/ml) | 0.49 ± 0.02 | 0.02 ± 0.01 | 0.94 ± 0.01 |
| anti-BSA (100 nM) | 0.34 ± 0.04 | 0.23 ± 0.02 | 0.33 ± 0.04 |
| anti-FITC (100 nM) | 0.58 ± 0.06 | 0.01 ± 0.01 | 0.96 ± 0.01 |
| anti-streptavidin (100 nM) | 0.57 ± 0.01 | 0.03 ± 0.01 | 0.94 ± 0.01 |

[a]Fractional transmittance was measured between cross-polars and 5CB anchored on the rubbed film of BSA after immersion in protein solutions for 2 hrs.
[b,c]The maximum values ($I_{Max}$) of fractional transmittance were measured when the angle between the polarizer and the rubbing direction of optical cell was 45°, 135°, 225° and 315°. The minimum values ($I_{Min}$) were obtained when its angle was 0°, 90°, 180° and 270°.
[d]The values of $[I_{Max} - I_{Min}]/I_{Max}$ were calculated from the paired fractional transmittances at (0°, 45°), (90°, 135°), (180°, 225°) and (270°, 315°).
[e]The reference indicates the rubbed films of immobilized BSA before the protein adsorption.

Rubbed Films of Biotin-BSA

Figure 7:
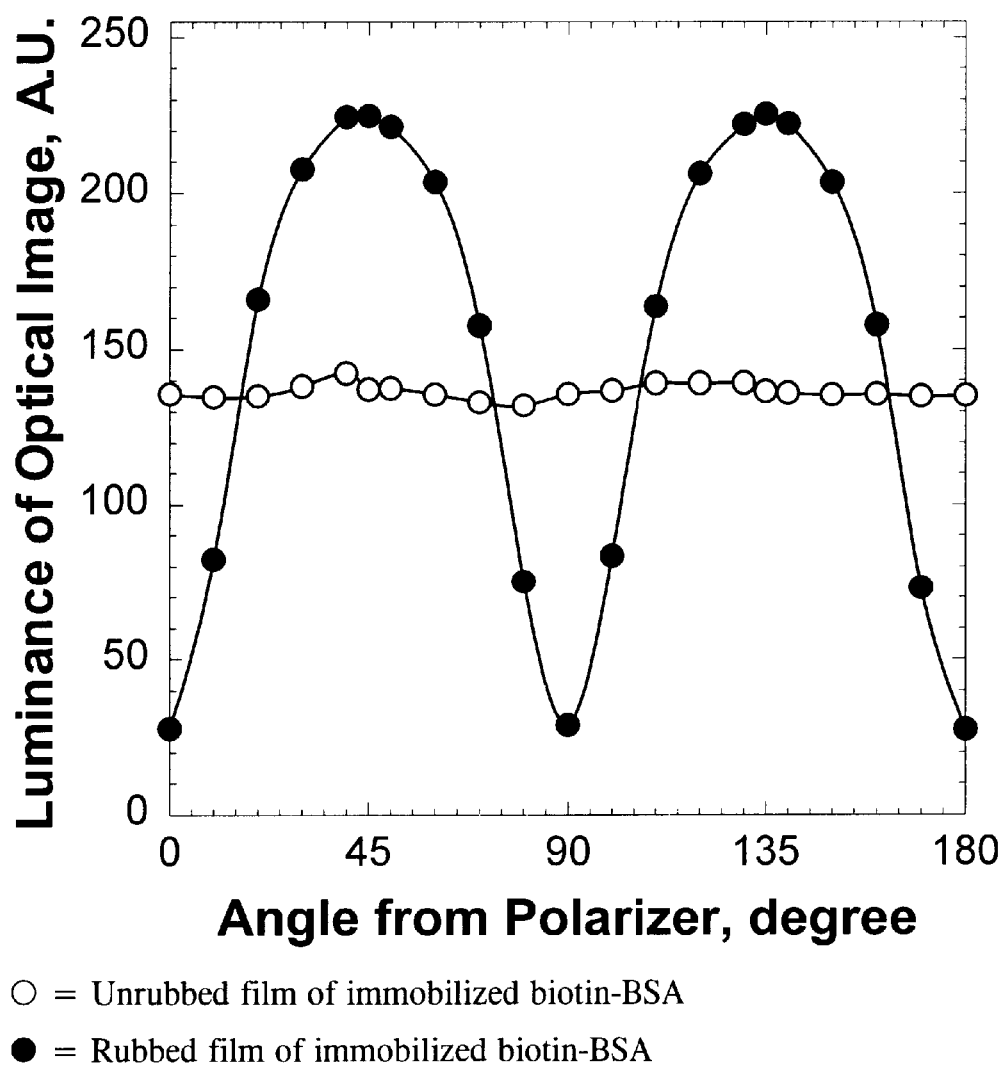
FIG. 7 is a graph showing the fractional transmittance of light between cross-polars and 5CB anchored on unrubbed (○) and rubbed (●) glass slides containing chemically-immobilized biotin-BSA prepared according to FIG. 1 using biotin-BSA rather than BSA. The fractional transmittance is shown as a function of the angle between the sample and the polarizer. The fractional transmittance is the ratio of the intensity of light transmitted through the optical cell containing the liquid crystal and between the cross-polars to the maximum intensity of light transmitted through an empty cell under parallel-polars.

Changes in the optical textures of 5CB in optical cells prepared from rubbed and unrubbed biotin-BSA substrates were observed and photographed ad described above. When rotated between crossed polarizers, little modulation, if any, in the optical texture was observed on the film of biotin-BSA that had not been rubbed indicating no uniform anchoring of the 5CB. In contrast, the optical appearance of 5CB anchored between the rubbed films was observed to modulate between dark and light by rotating the cell between crossed polarizers. These differences are graphically illustrated in FIG. 7. A comparison of FIG. 4 with FIG. 7 shows that optical cells prepared from rubbed and unrubbed biotin-BSA substrates behaved similarly to those prepared from rubbed and unrubbed BSA substrates with respect to ability to uniformly anchor the liquid crystal. As was the case for the optical cells prepared from BSA substrates, the liquid crystals appear dark when the optical axis of the nematic phase aligns with either the polarizer or the analyzer for the optical cells prepared from biotinylated BSA. When the direction of rubbing (i.e., optical axis of the nematic phase of 5CB) was aligned parallel to either the polarizer or the analyzer, the polarization of the incident light was not changed by transmission through the cell. The optical appearance of the liquid crystal was, therefore, uniformly dark when viewed through crossed polarizers. However, the rotation of cell allowed the incident light to pass through crossed polarizers by changing the polarization of light, and the intensity of passed light reached maximum at 45° rotation of rubbing direction to polarizer. FIG. 7 summarizes the trends in the average luminance of biotin-BSA films as a function of the rotation angles of the cell. As shown in FIG. 7, the sample prior to rubbing didn't show any modulation when the cell was rotated, but a pronounced periodic and strong modulation in the rubbed sample was observed. Maximum luminance was observed 45°, 135°, 225°, and 315° and minimum luminance was observed at 0°, 90°, 180°, and 270°.

Optical Textures of Liquid Crystals by Bound Anti-Biotin IgG on Rubbed Films of Biotin-BSA Initially, standard rubbing conditions (1 minute rubbing with ~2.1 mm/sec of rubbing speed and ~1,000 Pa of applied pressure) were used to evaluate chemically immobilized biotin-BSA substrates. Under these conditions the optical textures of optical cells prepared from rubbed biotin-BSA substrates was found to depend on the concentration of anti-biotin IgG in the solution the substrates were immersed in. The optical appearance of the liquid crystals became more complex and non-uniform as the concentration of anti-biotin IgG in the analyte solution increased. At low concentrations, the uniform alignment was first observed by the appearance of disclination lines which make the light scatter. Even though the number of disclination loops increased with concentration, the rotation of the sample still produced quite strong modulations in the intensity of light transmitted through the optical cells. As the concentration of anti-biotin IgG increased further, the appearance of highly non-uniform textures of the supported liquid crystals was observed until, finally, the rotation of these samples led to little measurable modulation in the intensity of light transmitted through the cells. The highly non-uniform appearance of the liquid crystals, indicates that the nematic phase of 5CB is anchored without a preferred azimuthal orientation on these films.

The sensitivity of optical texture to binding of anti-biotin IgG in solution was explored. Specifically, films of biotin-BSA were rubbed under different conditions to discover what role, if any, rubbing conditions had on sensitivity. Control of sensitivity in the detection of IgG is important. If detection sensitivity can be altered, the flexibility in the detection range in bioassay applications can be afforded. First, the applied pressure was decreased from 1,000 to 250 Pa without changing the other rubbing parameters. The results of rubbing the biotin-BSA substrate with the lower mass were that the uniform anchoring of 5CB was erased at lower concentrations of anti-biotin IgG. For example, biotin-BSA substrates rubbed at reduced pressure (~250 Pa) exhibited highly non-uniform textures when exposed to solutions of anti-biotin IgG at a concentration of 20 nM. Contrastingly, uniform alignment of 5CB was retained when similar substrates rubbed under the same conditions except with a pressure of ~1,000 Pa were incubated in anti-biotin IgG solutions at a concentration 28 nM. Thus, the sensitive of detection systems and optical cells prepared from rubbed substrates can be increased by decreasing the rubbing pressure. Changing the other rubbing conditions was found to similarly modify sensitivity. For example, reducing the rubbing time from 60 to 24 seconds in addition using an applied rubbing pressure of 250 Pa increased sensitivity even more. These results demonstrate that the sensitivity of rubbed films can be controlled by simply changing the rubbing conditions. As a control experiment, rubbed films of biotin-BSA were prepared using three rubbing conditions. The rubbing speed, length, and pressure in these experiments were approximately 2.1 mm/second, 127 mm, and 1,000 Pa; 2.1 mm/second, 127 mm, and 250 Pa; and 2.1 mm/second, 51 mm, and 250 Pa. Rubbed biotin-BSA substrates prepared using these conditions were incubated in PBS buffered solutions that did not contain any anti-biotin IgG. The rubbing made the optical textures of 5CB uniform (featureless), and optical cells prepared from the rubbed substrates were difficult to differentiate. Although the appearance of some disclination loops was observed in the optical cells prepared from rubbed substrates in which the rubbing pressure and length were reduced, the optical textures retain enough uniform alignment so that they may be differentiated from optical cells with non-uniformity resulting from specific binding of anti-biotin IgG. This indicates that sensitivity can be increased without giving false positive test results.

Figure 8:
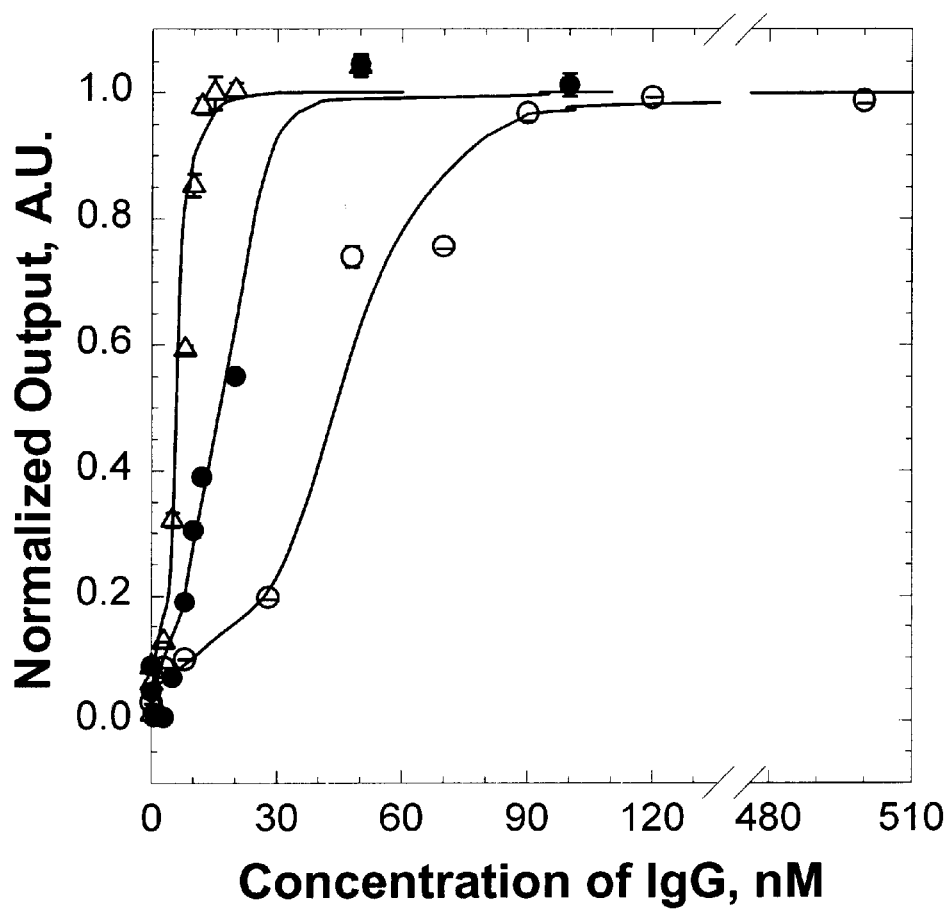
FIG. 8 is a graph showing the normalized optical outputs of 5CB anchored on rubbed films of biotin-BSA as a function of the concentration of anti-biotin IgG. The rubbing speed, length, and pressure were approximately 2.1 mm/second, 127 mm, and 1,000 Pa (○); 2.1 mm/second, 127 mm, and 250 Pa (●); and 2.1 mm/second, 51 mm, and 250 Pa (△).

Quantitative Analysis of the Optical Appearance of 5CB Induced by Binding of Anti-Biotin IgG Changes in the optical appearance of optical cells formed from the rubbed substrates of biotin-BSA upon exposure to concentrations of anti-BSA immunoglobulin were quantified by measuring the average luminance of optical texture using the methods described above. The corrected and normalized optical output can be expressed by the following equation:

$$\text{Normalized Output} = \frac{S - S_{\text{Min}}}{S_{\text{Max}} - S_{\text{Min}}} \quad (1)$$

where, S is the maximum luminance ratio between dark and bright images obtained from rotating the cell ($L_{Min}/L_{Max}$), $L_{Min}$ is the average luminance of the texture when the rubbing direction is parallel to the polarizer between crossed polarizers, $L_{Max}$ was obtained when the rubbing direction was rotated 45° with respect to the polarizer, and $S_{Max}$ and $S_{Min}$ are obtained using the films of biotin-BSA prior to and after rubbing. The normalized optical output using the luminance ratio (S) and the reference cells, provided quantitative information about the degree of non-uniformity that resulted upon incubation in solutions with varying amount of anti-biotin IgG. The amount of variation found from point to point or sample to sample could also be minimized. FIG. 8 shows the normalized optical outputs obtained from images of liquid crystals supported on the rubbed films of biotin-BSA after specific binding of anti-biotin IgG as a function of concentration of the immunoglobulin. FIG. 8 demonstrates that that a decrease in rubbing strength and length moved the threshold between uniform and non-uniform alignment of liquid crystals into lower concentrations of the immunoglobulin. A more detailed inspection of the non-uniform features using the optical output can be performed by measuring the amount of bound anti-biotin IgG on the rubbed films as described below.

Bound Anti-Biotin IgG on Rubbed Films of Biotin-BSA

Figure 9:
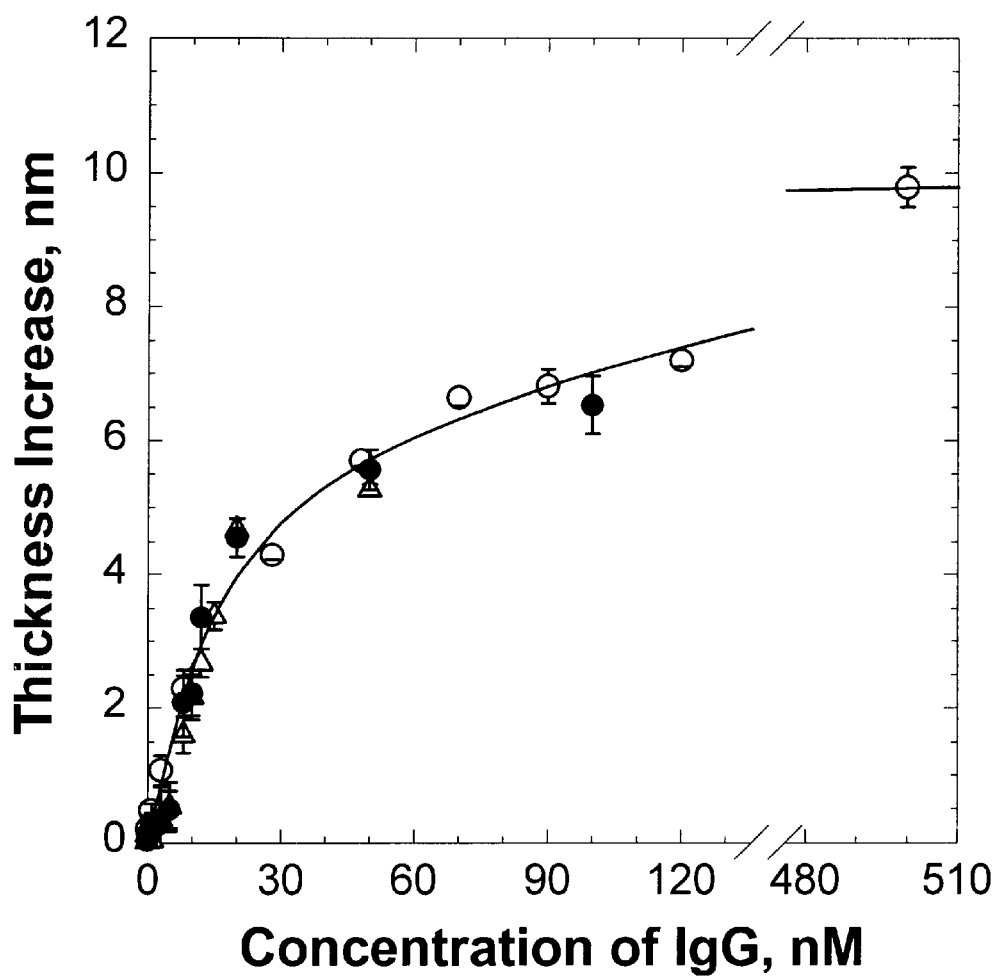
FIG. 9 is a graph showing the ellipsometric thicknesses of films of biotin-BSA covalently immobilized on the surface of a silicon wafer (with native oxide) as a function of the concentration of anti-biotin IgG in solution. The rubbing speed, length and pressure were approximately 2.1 mm/second, 127 mm, and 1,000 Pa (○); 2.1 mm/second, 127 mm, and 250 Pa (●); and 2.1 mm/second, 51 mm, and 250 Pa (△).

To evaluate the amount of anti-biotin IgG bound specifically on the rubbed biotin-BSA layer, the thickness increase resulting from bound IgG on rubbed films of biotin-BSA immobilized on silicon wafers was measured using ellipsometric thickness measurement techniques as described above (FIG. 9). FIG. 9 shows that the increase in thickness resulting from the binding of anti-biotin IgG was almost the same for each of the substrates despite the different rubbing conditions. This was true even though, as noted above and illustrated in FIG. 8, the normalized optical outputs were strongly influenced by the changes in rubbing conditions. As shown in FIG. 9, the thickness of bound anti-biotin IgG increased gradually and reached saturation at about 10 nm. Considering the size of IgG, generally estimated to be 4 nm×10 nm×14 nm, the saturation thickness increase of about 10 nm indicated that the surface was almost completely covered by anti-biotin IgG at saturation.

Figure 10:
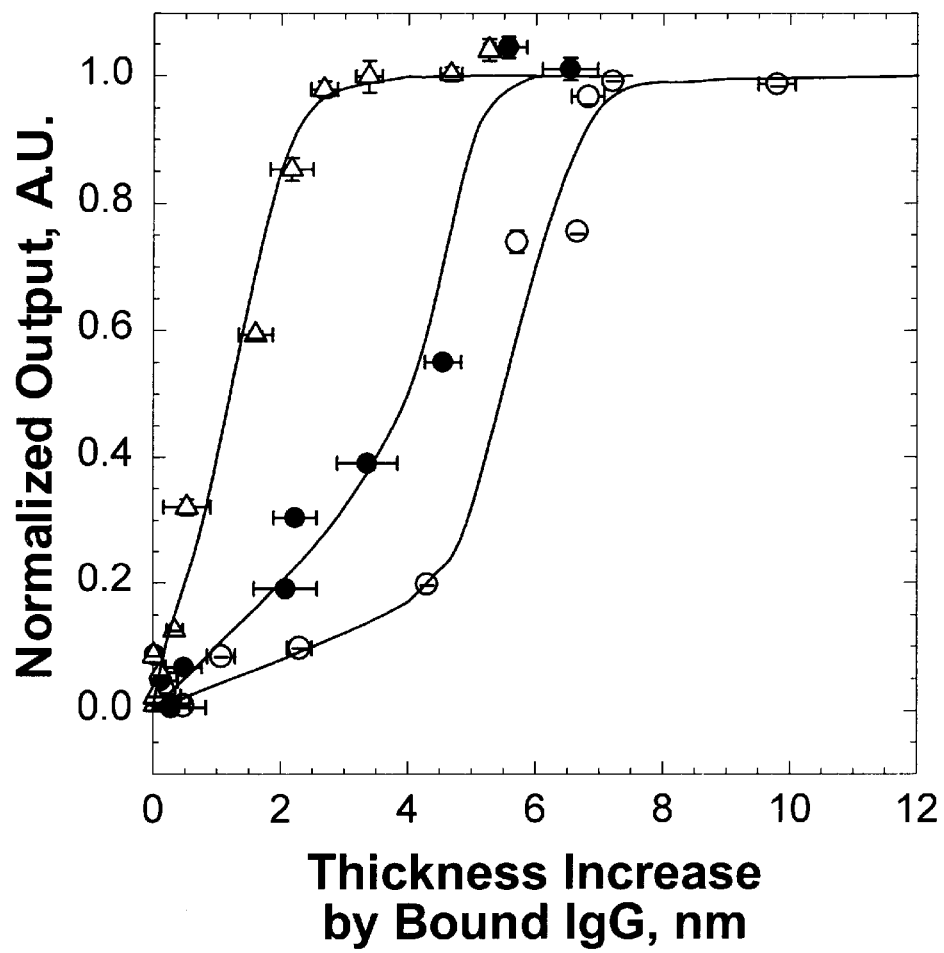
FIG. 10 is a graph showing the normalized optical outputs of 5CB anchored on rubbed films of biotin-BSA as a function of the amount of anti-biotin IgG bound to the films of biotin-BSA. The rubbing speed, length and pressure were approximately 2.1 mm/second, 127 mm, and 1,000 Pa (○); 2.1 mm/second, 127 mm, and 250 Pa (●); and 2.1 mm/second, 51 mm, and 250 Pa (△).

As described above and shown in FIG. 8, the optical textures and normalized optical output measurements described provided the concentrations of anti-biotin IgG at amount that erased the uniform alignment of liquid crystals. As also noted above and shown in FIG. 9, measurements of the thickness of bound anti-biotin IgG provided the threshold amounts at levels that would retain or erase uniform alignment of 5CB by bound IgG. An inspection of FIGS. 8 and 9 thus shows the amount of bound anti-biotin IgG required to change the orientation property of liquid crystals anchored on the rubbed films. FIG. 10 demonstrates that the amount of bound anti-biotin IgG resulting from specific binding to the biotin on the biotin-BSA rubbed substrate surface triggers the increase in non-uniform anchoring of liquid crystals on the rubbed substrates. At standard rubbing conditions (2.1 mm/second, 127 mm (rubbing time of 1 minute), and a rubbing pressure of approximately 1,000 Pa (an aluminum block with a mass of approximately 200 grams and dimensions of 2.54 cm by 7.62 cm)), an abrupt change in optical output was observed at around 5 nm of bound anti-biotin IgG. A decrease in rubbing strength shifted the threshold to lower levels of bound anti-biotin IgG. When the rubbing pressure was decreased to 250 Pa, the threshold thickness shifted to around 4 nm of bound anti-biotin IgG. A decrease in both rubbing pressure from 1,000 Pa to about 250 Pa and in rubbing time from 60 to 24 seconds shifted the threshold amount from about 5 nm to less than 2 nm of bound anti-biotin IgG. Therefore, control of sensitivity in optical output of liquid crystals by bound proteins can be achieved by simply changing in rubbing conditions. Thus, rubbed substrates may be prepared for quantitative and qualitative use at various concentrations of target species.

Sensitivity in Optical Response by Changing Rubbing Conditions

The nature of the alignment of the liquid crystals with respect to rubbing conditions was examined using a systematic approach. To do this, the rubbing speed, the rubbing pressure and the rubbing length (i.e. rubbing time) were again varied. The standard rubbing conditions described above were used as a reference. One rubbing parameter at a time was changed so that its effect on sensitivity and thickness could be independently observed. When the rubbing conditions were altered over the ranges shown in FIGS. 11 and 12, the rubbing produced substrates that gave very uniform texture on exposure to 5CB (prior to incubation with the targeted analyte). Additionally, strong modulation was observed on rotating the cell similar to that shown in FIGS. 4 and 7. In order to observe the normalized optical output caused by specific binding of anti-biotin IgG as a function of rubbing condition, the rubbed substrates were incubated in solutions of anti-biotin IgG at a concentration of 20 nM which showed an intermediate state of optical output for substrates rubbed under standard conditions. This allowed the variation in optical image via changing rubbing condition to be specifically examined.

Figure 11:
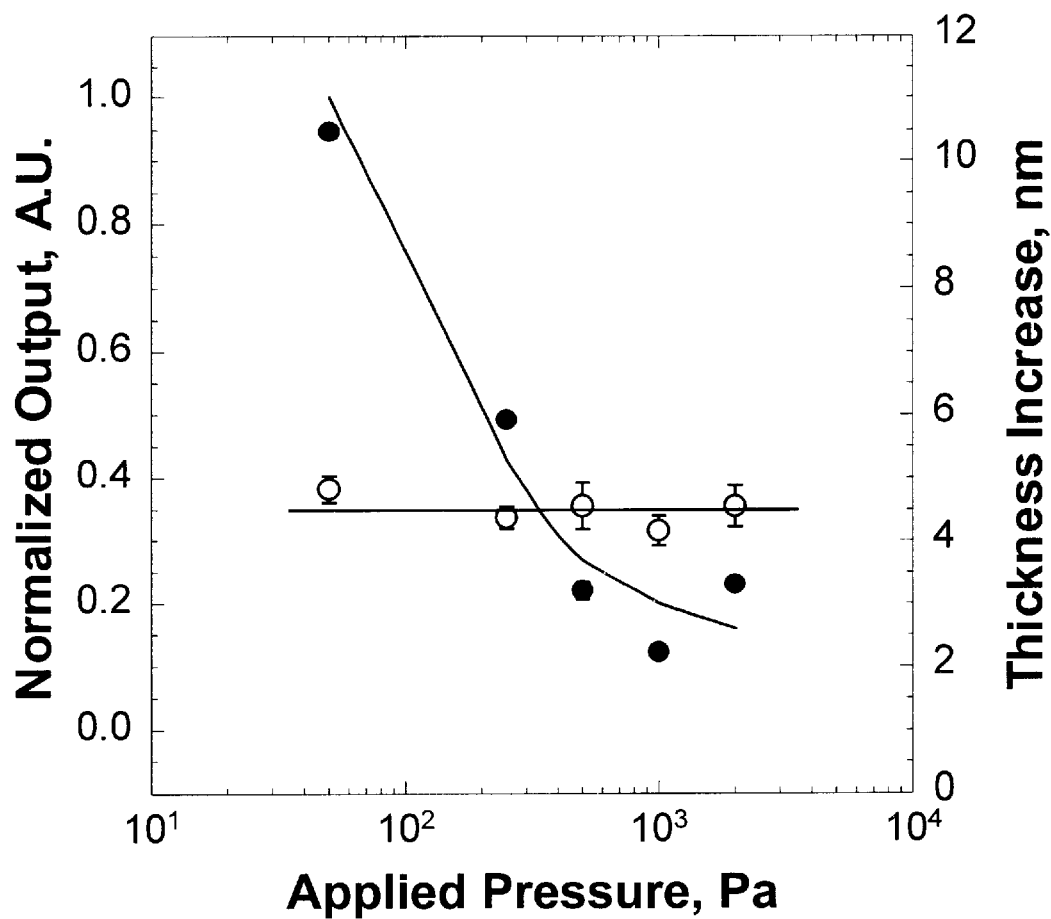
FIG. 11 is a graph showing the normalized optical outputs of a film of 5CB on rubbed films of biotin-BSA (●) and its correspondent increase in thickness (○) as a function of rubbing pressure. The rubbing speed and length were respectively approximately 2.1 mm/second and 127 mm. The rubbed films were immersed in PBS solutions of 20 nM anti-biotin IgG for 90 minutes with stirring.
Figure 12:
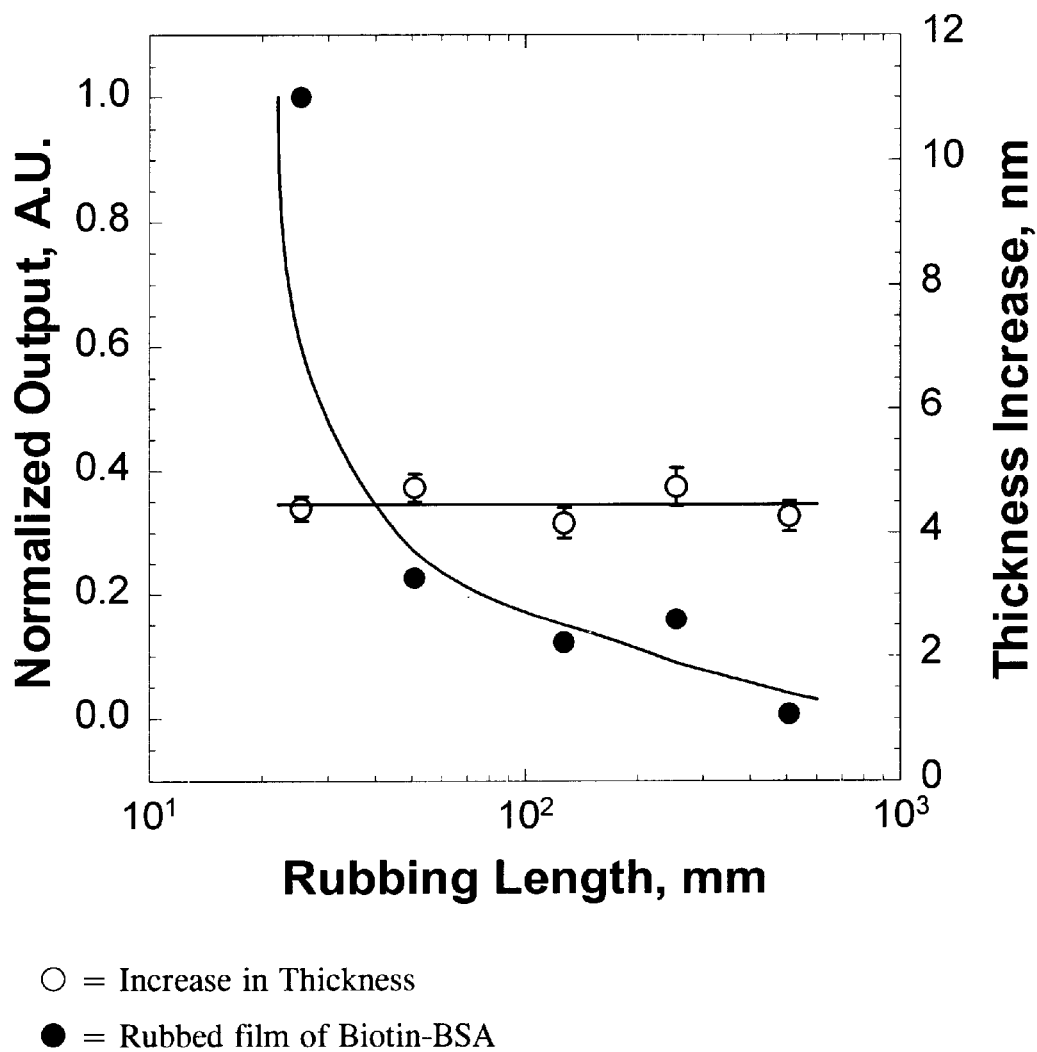
FIG. 12 is a graph showing the normalized optical outputs of a film of 5CB on rubbed films of biotin-BSA (●) and its correspondent increase in thickness (○) as a function of rubbing length. The rubbing speed and pressure were approximately 2.1 mm/second and 1,000 Pa. The rubbed films were immersed in PBS solutions of 20 nM anti-biotin IgG for 90 minutes with stirring.

FIG. 11 shows how the amount of bound anti-biotin IgG as indicated by the thickness increase and the normalized optical output changed after incubation in a solution of anti-biotin IgG at a concentration of 20 nM as a function of pressure applied during rubbing. FIG. 12 shows how the rubbing length impacted the same parameters. When standard rubbing conditions were used, incubation of the rubbed films of biotin-BSA in 20 nM anti-biotin IgG solution produced about 4 nm of bound IgG (FIG. 9), the appearance of some disclination loops, and a normalized optical output of around 0.2 (FIG. 8). As shown in FIGS. 11 and 12, after incubation in the anti-biotin IgG solution no detectable change in thickness occurred as a result of changes in the pressure or rubbing length used during rubbing. However, the optical output was strongly affected by the rubbing conditions used to prepare the rubbed substrate. Therefore, the pressure applied during the rubbing process can be used to alter the sensitivity of an optical cell prepared from a rubbed substrate. FIG. 12 shows that the rubbing length significantly impacts the optical appearance even over a short range of rubbing length while the thickness is unaffected. The decrease in the rubbing length increased non-uniformity in the optical texture, and completely non-uniform features were obtained at a rubbing length of 2.54 mm. An increase in rubbing length made the rubbed film resist non-uniform anchoring of 5CB. Thus, when the rubbing length was increased to ~508 mm, the optical appearance of the rubbed film incubated with the anti-biotin IgG showed perfectly uniform texture and its normalized optical output was almost zero. This means that incubation in the 20 nM solution of anti-biotin IgG produced almost no change in the optical texture of the rubbed substrate. The effects of rubbing speed on thickness increase and normalized output were also examined. However, little change in optical output was observed as a function of rubbing speed. These results demonstrate that rubbing pressure and rubbing length are very effective parameters that may be used to control and modify sensitivity in optical cells prepared using rubbed substrates.

Based on the above results, image analysis of the optical output of liquid crystals on rubbed films of biotin-BSA can be used to quantitatively determine the amount of anti-biotin IgG bound to the surface of the rubbed biotin-BSA substrate. Additionally, such substrates may be used to determine the presence of and amount of a substance such in a sample as demonstrated with anti-biotin IgG. Furthermore, the sensitivity of the optical output can be easily controlled by modifying the rubbing conditions used in preparing the rubbed substrate. Thus, rubbed substrates are useful for imaging specific biomolecular interactions when used in conjunction with liquid crystals.

Preparation of Rubbed Substrates with Antibodies

As noted above, various procedures may be used to prepare rubbed substrates containing antibodies as the biomolecule recognition agent. A summary of six such procedures follows:

Procedure 1
1. Covalently immobilize the antibody on the surface of a glass microscope slide using a DSS activated glass slide by immersing the activated glass in an aqueous solution of the antibody.
2. Mechanically rub the surface of the slide containing the immobilized antibody using a modified chart recorder
3. Block the rubbed protein film by immersing it in a 10 mg/mL BSA aqueous solution for 1 hour.

Procedure 2
1. Covalently immobilize the antibody on the surface of a glass microscope slide using a DSS activated glass slide by immersing the activated glass in an aqueous solution of the antibody.
2. Block the substrate by immersing it in a 10 mg/mL BSA aqueous solution for 1 hour.
3. Mechanically rub the immobilized antibody/BSA surface using a modified chart recorder.
4. Block the rubbed protein film by immersing it in a 10 mg/mL BSA aqueous solution for 1 hour.

Procedure 3
1. Covalently immobilize a protein to a DSS activated glass microscope by immersing the activated glass slide in an aqueous solution of the protein.
2. Bind an antibody specific to the immobilized protein to the immobilized protein by immersing the substrate in an aqueous solution of the antibody.
3. Mechanically rub the surface of the substrate containing the immobilized antibody and protein using a modified chart recorder.
4. Block the rubbed protein surface on the substrate by immersing it in a 10 mg/mL aqueous solution of BSA for one hour.

Procedure 4
1. Covalently immobilize a protein to a DSS activated glass microscope by immersing the activated glass microscope slide in an aqueous solution of the protein.
2. Mechanically rub the surface containing the immobilized protein using a modified chart recorder.
3. Bind an antibody specific to the immobilized protein to the immobilized protein by immersing the slide in an aqueous solution of the antibody.
4. Block the rubbed protein film by immersing it in a 10 mg/mL BSA aqueous solution for one hour.

Procedure 5
1. Covalently immobilize BSA on a DSS activated glass microscope slide by immersing the slide in an aqueous solution of BSA.
2. Mechanically rub the surface of the immobilized BSA using a modified chart recorder.
3. Covalently immobilize an antibody to the immobilized BSA using DSS to reactivate the surface.
4. Block the surface of the rubbed substrate by immersing it in a 10 mg/mL BSA aqueous solution for 1 hour.

Procedure 6
1. Covalently immobilize BSA on a DSS activated glass microscope slide by immersing the slide in an aqueous solution containing BSA.
2. Covalently immobilize an antibody on the immobilized BSA surface using DSS to reactivate the surface.
3. Mechanically rub the surface containing the immobilized antibody and BSA using a modified chart recorder.
4. Block the rubbed substrate surface immersing it in a 10 mg/mL BSA aqueous solution for one hour.

Preparation of Rubbed Protein Substrates with Nitrilotriacetate/$Ni^{+2}$

Several procedures may be used to prepare rubbed substrates with nitriliotriacetate(NTA)/$Ni^{+2}$. Such rubbed substrates are useful for detecting histidine fusion proteins.

In a first procedure, NTA-functionalized BSA is covalently immobilized on a glass microscope slide using DSS by immersing the slide in a solution containing 10 mg/mL of NTS-functionalized BSA for a period of one hour. The slide is then dried and mechanically rubbed using a modified chart recorder such as described above. The NTS-BSA film is then immersed in an aqueous solution comprising $Ni^{+2}$ to form the complex.

In a second procedure, BSA is first covalently immobilized on the surface of a glass microscope slide by immersing the slide in a solution of 10 mg/mL BSA for one hour. The surface of the slide is then rubbed using the modified strip chart recorder. The rubbed surface is then activated with DSS, and the activated substrate is incubated with NTA-ligand such as an amino-terminated NTA available from Qiagen using a solution of NTA-ligand with a concentration of about 1 mM for about six hours. The resulting substrate is then immersed in a 10 mg/mL solution of BSA for one hour to block the surface. The resulting substrate is then immersed in an aqueous solution containing $Ni^{+2}$ at a concentration of about 10 mM for three hours.

In a third procedure, BSA is first covalently immobilized on the surface of a glass slide by immersing the slide for one hour in an aqueous solution containing about 10 mg/mL BSA. Next, the surface of the BSA-coated substrate is activated using DSS as described above. The activated BSA-coated substrate is then incubated in a 1 mM solution of NTA-ligand for a period of about 6 hours. Subsequently, the substrate is immersed in a 10 mg/mL aqueous solution of BSA to block the surface. After the surface is blocked, the substrate is immersed in an aqueous solution with a concentration of $Ni^{+2}$ of about 10 mM for a period of about three hours. Finally, the surface of the resulting substrate is mechanically rubbed using the procedures described above.

One skilled in the art will immediately recognize that the rubbed substrates of the present invention may be used to detect a wide variety of target species and that a wide variety of biomolecule recognition agents may be used in the rubbed substrates. A non-exhaustive list of just some of the biomolecule recognition agents and target species for use in accordance with the present invention follows:

| Biomolecule recognition agent | Target species |
| --- | --- |
| Anti-Ras IgG | Ras |
| Histidine fusion of RAF1 | Activated Ras |
| RAF1 | Activated Ras |
| GST fusion of RAF1 | Activated Ras |
| Sialic acid | Influenza virus |
| Anti-active p38, pAb, Rabbit (pTGpY) | p38 |
| Anti-pT183 MAPK pAb, Rabbit | MAPK |
| Anti-active MAPK, pAb, Rabbit, (pTEpY) | Activated MAPK |
| Anti-ERK ½ pAb, Rabbit | ERK |
| Anti-active JNK pAb, Rabbit, (pTPpY) | Activated JNK |
| Anti-active CaM MI pAb, Rabbit, (pT286) | Activated CaM KII |
| Anti-pS473 Akt, pAb | Akt |
| Anti-Phosphotyrosine pAb | Phosphotyrosine |
| Donkey Anti-Rabbit IgG, | Rabbit IgG |
| Mannose | Concavalin A |
| Anti-Hepatitis C IgG | Hepatitis C virus |
| Anti-Hepatitis B IgG | Hepatitis B virus |
| Anti-active p38 pAb | Activated p38 |
| Anti-CNP mAb | CNP |
| Anti-GBP pAb | GBP |
| Anti-Human BDNF pAb | BDNF |
| Anti-Human GDNF pAb | GDNF |
| Anti-Human NT-3 pAb | NT-3 |
| Anti-Human NT-4 pAb | NT-4 |
| Anti-Human p75 pAb | p75 |
| Anti-Human Tryptase mAb | Tryptase |
| Anti-NGF mAb | NGF |
| Anti-Pan Trk pAb | Trk |
| Anti-Rat CNTF pAb | CNTF |
| Anti-TrkB In pAb | TrkB |
| Anti-TGF-b1 pAb | TGF-b1 |
| Anti-VACht pAb | VACht |
| Anti-GFP | Green Fluorescent protein |
| NIA-Ni | Histidine fusion proteins |
| Glutathione | GST fusion proteins |

It is understood that the invention is not limited to the embodiments set forth herein for illustration, but embraces all such forms thereof as come within the scope of the following claims.

What is claimed is:
1. A rubbed substrate structure for use in a liquid crystal assay device, comprising:
(a) a biochemical blocking compound chemically i mobilized on a support thereby forming a biochemical blocking layer; and
(b) a biomolecule recognition agent deposited on the same side of the support as the biochemical blocking layer,
wherein a surface of the biochemical blocking layer is rubbed surface that possesses features that drive a uniform anchoring of liquid crystals Is when the liquid crystals contact the rubbed surface,
wherein the biochemical blocking layer resists non-specific adsorption of non-target species, wherein the biomolecule recognition agent is immobilized on the support by being bonded to the biochemical blocking compound, and further wherein the biomolecule recognition agent comrises a recognition site capable of selectively recognizing a target species.

2. The rubbed substrate structure for use in a liquid crystal assay device according to claim 1, wherein the biomolecule recognition agent is deposited on the rubbed surface.

3. The rubbed substrate structure for use in a liquid crystal assay device according to claim 1, wherein the biomolecule recognition agent is deposited on the same side of the support as the biochemical blocking layer before the biochemical blocking layer is rubbed.

4. The rubbed substrate structure for use in a liquid crystal assay device according to claim 1, wherein the biochemical blocking compound is immobilized on the support by crosslinking with a crosslinking agent.

5. The rubbed substrate structure for use in a liquid it crystal assay device according to claim 4, wherein the crosslinking gent is glutaraldehyde.

6. The rubbed substrate structure for use in a liquid crystal assay device according to claim 1, wherein the biochemical locking compound is immobilized on the support by being bonded to a bifunctional spacer compound, wherein the bifunctional spacer compound is bonded to a surface modifying compound and the surface modifying compound is bonded to a functionality on the surface of the support.

7. The rubbed substrate structure for use in a liquid crystal assay device according to claim 1, wherein the biochemical blocking compound comprises a serum albumin and the biomolecule recognition agent i an immunoglobulin, a portion of an immunoglobulin, a peptide, a polypeptide, a carbohydrate, a fragment of RNA, or a fragment of DNA.

8. The rubbed substrate structure for use in a liquid crystal assay device according to claim 1, wherein the biochemical locking compound comprises bovine serum albumin and the biomolecule recognition agent is capable of recognizing and binding peptides, polypeptides, DNA, RNA, DNA fragments, RNA fragments or a binding domain associated with a protein, a virus, a bacteria, or a microscopic pathogen.

9. The rubbed substrate structure for use in a liquid crystal assay device according to claim 1, wherein at lea t two regions of the rubbed surface are rubbed under different pressures, speeds, or for different lengths whereby the at least two regions of the rubbed surface have different sensitivities towards the target species.

10. A kit for use in a liquid crystal assay, comprising:

(a) at least one rubbed substrate structure according to claim 1;

(b) a second surface that uniformly anchors liquid crystals;

(c) a spacing material adapted to be placed between the rubbed substrate and the second surface that uniformly anchors liquid crystals; and (d) a liquid crystal compound.

11. The kit for use in a liquid crystal assay according to claim 10, wherein the liquid crystal is 4-cyano-4'-pentylbiphenyl.

12. The kit for use in a liquid crystal assay according to claim 10, wherein the at least one rubbed substrate structure, the second surface that uniformly anchors liquid crystals, and the spacing material are preassembled into an optical cell.

13. A kit for use in detecting the presence of a target species in a sample, the kit comprising: at least one rubbed substrate structure according to claim 1 and a liquid crystal compound.

14. The rubbed substrate structure for use in a liquid crystal assay device according to claim 1, wherein the biochemical blocking layer is a serum albumin.

15. The rubbed substrate structure for use in a liquid crystal assay device according to claim 14, wherein the serum albumin is bovine serum albumin.

16. The rubbed substrate structure for use in a liquid crystal assay device according to claim 14, wherein the serum albumin is human serum albumin, rodent serum albumin, canine serum albumin, feline serum albumin, porcine serum albumin, equine serum albumin or rabbit serum albumin.

17. The rubbed substrate structure for use in a liquid crystal assay device according to claim 1, wherein the sup ort comprises glass.

18. The rubbed substrate structure for use in a liquid crystal assay device according to claim 1, wherein the support comprises silica.

19. The rubbed substrate structure for use in a liquid crystal assay device according to claim 1, wherein the biomolecule recognition agent comprises a portion of an immunoglobulin, a peptide, a protein, a carbohydrate, a fragment of RNA or a fragment of DNA.

* * * * *

UNITED STATES PATENT AND TRADEMARK OFFICE
CERTIFICATE OF CORRECTION

PATENT NO. : 6,692,699 B2  
DATED : February 17, 2004  
INVENTOR(S) : Nicholas Lawrence Abbott and Seung-Ryeol Kim It is certified that error appears in the above-identified patent and that said Letters Patent is hereby corrected as shown below:

Column 14,
Line 5, "N-succininidyl" should be -- N-succinimidyl --.

Column 38,
Line 11 of the table, "Anti-active CaM MI pAb, Rabbit (pT286)" should be -- Anti-active CaM KII pAb, Rabbit (pT286) --.
Line 57, "i mobi-" should be -- immobi- --.
Line 63, "layer is" should be -- layer is a --.
Line 64, "crystals Is when" should be -- crystals when --.

Column 39,
Line 19, "it" should be deleted.
Line 21, "gent" should be -- agent --.
Line 24, "locking" should be -- blocking --.
Line 32, "i an" should be -- is an --.
Line 37, "locking" should be -- blocking --.
Line 43, "lea t" should be -- least --.

Column 40,
Lines 36-37, "sup ort" should be -- support --.

Signed and Sealed this

Twenty-eighth Day of June, 2005

JON W. DUDAS  
*Director of the United States Patent and Trademark Office*